United States Patent
Simanzhenkov et al.

(10) Patent No.: US 10,626,066 B2
(45) Date of Patent: Apr. 21, 2020

(54) HIGH CONVERSION AND SELECTIVITY ODH PROCESS

(71) Applicant: NOVA Chemicals (International) S.A., Fribourg (CH)

(72) Inventors: Vasily Simanzhenkov, Calgary (CA); Shahin Goodarznia, Calgary (CA); Xiaoliang Gao, Calgary (CA); Kamal Serhal, Calgary (CA); Leonid Kustov, Moscow (RU); Aleksey Kucherov, Moscow (RU); Elena Finashina, Moscow (RU)

(73) Assignee: NOVA Chemicals (International) S.A., Fribourg (CH)

( * ) Notice: Subject to any disclaimer, the term of this patent is extended or adjusted under 35 U.S.C. 154(b) by 0 days.

(21) Appl. No.: 15/514,841

(22) PCT Filed: Oct. 8, 2015

(86) PCT No.: PCT/IB2015/057711
§ 371 (c)(1),
(2) Date: Mar. 28, 2017

(87) PCT Pub. No.: WO2016/059518
PCT Pub. Date: Apr. 21, 2016

(65) Prior Publication Data
US 2017/0210685 A1    Jul. 27, 2017

(30) Foreign Application Priority Data
Oct. 15, 2014    (CA) ...................... 2867731

(51) Int. Cl.
C07C 5/48    (2006.01)
B01J 8/18    (2006.01)
(Continued)

(52) U.S. Cl.
CPC ............... *C07C 5/48* (2013.01); *B01J 8/1818* (2013.01); *B01J 8/20* (2013.01); *B01J 8/228* (2013.01);
(Continued)

(58) Field of Classification Search
None
See application file for complete search history.

(56) References Cited

U.S. PATENT DOCUMENTS

| 2,395,362 A | 2/1946 | Welling |
| 3,420,911 A | 1/1969 | Woskow et al. |

(Continued)

FOREIGN PATENT DOCUMENTS

| CA | 2 415 064 A1 | 6/2004 |
| GB | 12 13 181 | 11/1970 |

(Continued)

OTHER PUBLICATIONS

Peri, J.B. and Hensley, A.L., Jr.; The Surface Structure of Silica Gel; The Journal of Physical Chemistry; vol. 72, No. 8, Aug. 1968; pp. 2926-2933.

(Continued)

*Primary Examiner* — Philip Y Louie
(74) *Attorney, Agent, or Firm* — Julie L. Heinrich

(57) ABSTRACT

Ethane may be catalytically oxidatively dehydrogenated to ethylene at high conversions and high selectivity in a circulating fluidized bed (CFB) reactor in the presence of oxygen in the feed in an amount above the flammability limit. The reactor has an attached regeneration reactor to regenerate the catalyst and cycle back to the CFB.

25 Claims, 12 Drawing Sheets

(51) Int. Cl.
  *B01J 8/38* (2006.01)
  *B01J 8/22* (2006.01)
  *B01J 8/20* (2006.01)
  *B01J 27/057* (2006.01)
  *B01J 27/30* (2006.01)
  *B01J 38/30* (2006.01)

(52) U.S. Cl.
  CPC ........... *B01J 8/388* (2013.01); *B01J 27/0576* (2013.01); *B01J 27/30* (2013.01); *B01J 38/30* (2013.01); *C07C 2523/20* (2013.01); *C07C 2523/22* (2013.01); *C07C 2523/28* (2013.01); *Y02P 20/52* (2015.11); *Y02P 20/584* (2015.11)

(56) References Cited

U.S. PATENT DOCUMENTS

| | | | |
|---|---|---|---|
| 3,420,912 | A | 1/1969 | Woskow et al. |
| 3,904,703 | A | 9/1975 | La et al. |
| 4,064,039 | A | 12/1977 | Penick |
| 4,072,600 | A | 2/1978 | Schwartz |
| 4,093,535 | A | 6/1978 | Schwartz |
| 4,250,346 | A | 2/1981 | Young et al. |
| 4,450,313 | A | 5/1984 | Eastman et al. |
| 4,524,236 | A | 6/1985 | McCain |
| 4,525,180 | A | 6/1985 | Hirai et al. |
| 4,596,787 | A | 6/1986 | Manyik et al. |
| 4,899,003 | A | 2/1990 | Manyik et al. |
| 4,917,711 | A | 4/1990 | Xie et al. |
| 5,011,591 | A | 4/1991 | Kuznicki |
| 5,202,517 | A | 4/1993 | Minet et al. |
| 5,365,006 | A * | 11/1994 | Serrand ................ B01J 8/067 422/139 |
| 5,565,399 | A | 10/1996 | Fraenkel et al. |
| 5,736,116 | A * | 4/1998 | LeBlanc ................ C01B 3/025 423/359 |
| 5,744,687 | A | 4/1998 | Ramachandran et al. |
| 5,859,304 | A | 1/1999 | Barchas et al. |
| 6,120,692 | A | 9/2000 | Wang et al. |
| 6,423,881 | B1 | 7/2002 | Yang et al. |
| 6,517,611 | B1 | 2/2003 | Kuznicki et al. |
| 6,518,476 | B1 | 2/2003 | Culp et al. |
| 6,521,808 | B1 | 2/2003 | Ozkan et al. |
| 6,566,573 | B1 | 5/2003 | Bharadwaj et al. |
| 6,581,476 | B1 | 6/2003 | Fremercy |
| 6,624,116 | B1 | 9/2003 | Bharadwaj et al. |
| 6,818,189 | B1 | 11/2004 | Adris et al. |
| 6,867,166 | B2 | 3/2005 | Yang et al. |
| 6,891,075 | B2 | 5/2005 | Liu |
| 7,319,179 | B2 | 1/2008 | Lopez Nieto et al. |
| 7,411,107 | B2 | 8/2008 | Lucy |
| 8,017,825 | B2 | 9/2011 | Kuznicki et al. |
| 8,107,825 | B2 | 1/2012 | Rajagopal et al. |
| 8,519,210 | B2 | 8/2013 | Arnold et al. |
| 9,550,709 | B2 | 1/2017 | Simanzhenkov et al. |
| 2004/0010174 | A1 | 1/2004 | Wang et al. |
| 2005/0089299 | A1 * | 4/2005 | Woodfin ................ C07C 5/333 385/147 |
| 2008/0194891 | A1 * | 8/2008 | Pretz ................ C07C 5/3332 585/252 |
| 2010/0256432 | A1 * | 10/2010 | Arnold ................ C07C 5/48 585/655 |
| 2011/0230698 | A1 * | 9/2011 | Towler ................ C07C 5/333 585/661 |
| 2011/0245571 | A1 | 10/2011 | Kustov et al. |
| 2011/0251047 | A1 * | 10/2011 | Niccum ................ B01J 23/40 502/38 |
| 2014/0275619 | A1 * | 9/2014 | Chen ................ C07C 51/215 562/512.2 |
| 2014/0371504 | A1 * | 12/2014 | Stine ................ C07C 5/48 585/658 |
| 2015/0045582 | A1 * | 2/2015 | Han ................ C07C 5/3332 562/549 |

FOREIGN PATENT DOCUMENTS

| | | |
|---|---|---|
| JP | 59172427 A | 9/1984 |
| WO | 02/30856 A1 | 4/2002 |
| WO | 2005/058498 A1 | 6/2005 |
| WO | 2006/130288 A1 | 12/2006 |

OTHER PUBLICATIONS

Wen, C.Y. and Yu, Y.H.; Mechanics of Fluidization; Chemical Engineering Progress Symposium Series; No. 62, vol. 62 (1966); pp. 100-111.

Al-Baghli, Nadhir A. and Loughlin, Kevin F.; Binary and Ternary Adsorption of Methane, Ethane, and Ethylene on Titanosilicate ETS-10 Zeolite; J. Chem. Eng. Data; Published on Web Nov. 24, 2005; Copyright American Chemical Society 2006, vol. 51, pp. 248-254.

* cited by examiner

HIGH CONVERSION AND SELECTIVITY ODH PROCESS

TECHNICAL FIELD

The present invention relates to oxidative dehydrogenation of lower paraffins in a high conversion and high selectivity process. To date the art has emphasized that oxidative dehydrogenation reactions must be carried out in a reaction mixture below the lower oxidative combustion limits. As the reaction is "oxygen starved" the conversion per pass tends to be low. However at the other end of the spectrum one might operate above the upper oxidative combustion limits. Such a process has very short dwell times in the reactor, for both the feed stream and the catalyst, and provides a once through high conversion and high selectivity process. Preferably the reaction is conducted in an apparatus of the design for a fluidized bed catalyst cracker.

BACKGROUND ART

The concept of oxidative dehydrogenation of paraffins to olefins (ODH) has been around since at least the late 1960's. Steam cracking of paraffins was a well established technology and commercially practiced well prior to the 1960's. The perceived benefit of ODH is lower operating temperatures which in turn reduce greenhouse gas emissions. The downside to ODH processes is the potential for a decomposition (decomp). Industrial scale facilities are expensive and corporations shy away from processes which may result in a decomp. As a result ODH technology has had a difficult time gaining traction.

There are a number of United States patents assigned to Petro-Tex Chemical Corporation issued in the late 1960's that disclose the use of various ferrites in a steam cracker to produce olefins from paraffins. The patents include U.S. Pat. Nos. 3,420,911 and 3,420,912 in the names of Woskow et al. The patents teach introducing ferrites such as zinc, cadmium, and manganese ferrites (i.e. mixed oxides with iron oxide). The ferrites are introduced into a dehydrogenation zone at a temperature from about 250° C. up to about 750° C. at pressures less than 100 psi (689.476 kPa) for a time less than 2 seconds, typically from 0.005 to 0.9 seconds. The reaction appears to take place in the presence of steam that may tend to shift the equilibrium in the "wrong" direction. Additionally the reaction does not take place in the presence of a catalyst.

GB 1,213,181, which seems to correspond in part to the above Petro-Tex patents, discloses that nickel ferrite may be used in the oxidative dehydrogenation process. The reaction conditions are comparable to those of above noted Petro-Tex patents.

U.S. Pat. No. 6,891,075 issued May 10, 2005 to Liu, assigned to Symyx Technologies, Inc. teaches a catalyst for the oxidative dehydrogenation of a paraffin (alkane) such as ethane. The gaseous feedstock comprises at least the alkane and oxygen, but may also include diluents (such as argon, nitrogen, etc.) or other components (such as water or carbon dioxide). The dehydrogenation catalyst comprises at least about 2 weight % of NiO and a broad range of other elements preferably Nb, Ta, and Co. While NiO is present in the catalyst it does not appear to be the source of the oxygen for the oxidative dehydrogenation of the alkane (ethane).

U.S. Pat. No. 6,521,808 issued Feb. 18, 2003 to Ozkan et al., assigned to the Ohio State University teaches sol-gel supported catalysts for the oxidative dehydrogenation of ethane to ethylene. The catalyst appears to be a mixed metal system such as Ni—Co—Mo, V—Nb—Mo possibly doped with small amounts of Li, Na, K, Rb, and Cs on a mixed silica oxide/titanium oxide support. Again the catalyst does not provide the oxygen for the oxidative dehydrogenation, rather gaseous oxygen is included in the feed.

U.S. Pat. No. 4,450,313, issued May 22, 1984 to Eastman et al., assigned to Phillips Petroleum Company discloses a catalyst of the composition $Li_2O$—$TiO_2$, which is characterized by a low ethane conversion not exceeding 10%, in spite of a rather high selectivity to ethylene (92%). The major drawback of this catalyst is the high temperature of the process of oxidative dehydrogenation, which is close to or higher than 650° C.

The preparation of a supported catalyst usable for low temperature oxy-dehydrogenation of ethane to ethylene is disclosed in the U.S. Pat. No. 4,596,787 A, issued Jun. 24, 1986 assigned to Union Carbide Corp. A supported catalyst for the low temperature gas phase oxydehydrogenation of ethane to ethylene is prepared by (a) preparing a precursor solution having soluble and insoluble portions of metal compounds; (b) separating the soluble portion; (c) impregnating a catalyst support with the soluble portion; and (d) activating the impregnated support to obtain the catalyst. The calcined catalyst has the composition $Mo_aV_bNb_cSb_dX_e$. X is nothing or Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U, Mn and/or W; a is 0.5-0.9; b is 0.1-0.4; c is 0.001-0.2; d is 0.001-0.1; e is 0.001-0.1 when X is an element. The patent fails to teach or suggest a co-comminution of the catalyst and the support.

Another example of the low temperature oxy-dehydrogenation of ethane to ethylene using a calcined oxide catalyst containing molybdenum, vanadium, niobium and antimony is described in the U.S. Pat. No. 4,524,236 A issued Jun. 18, 1985 and U.S. Pat. No. 4,250,346 A issued Feb. 10, 1981, both assigned to Union Carbide Corp. The calcined catalyst contains $Mo_aV_bNb_cSb_dX_e$ in the form of oxides. The catalyst is prepared from a solution of soluble compounds and/or complexes and/or compounds of each of the metals. The dried catalyst is calcined by heating at 220-550° C. in air or oxygen. The catalyst precursor solutions may be supported onto a support, e.g. silica, aluminum oxide, silicon carbide, zirconia, titania or mixtures of these. The selectivity to ethylene may be greater than 65% for a 50% conversion of ethane.

The U.S. Pat. No. 6,624,116, issued Sep. 23, 2003 to Bharadwaj et al. and U.S. Pat. No. 6,566,573 issued May 20, 2003 to Bharadwaj et al., both assigned to Dow Global Technologies Inc. disclose Pt—Sn—Sb—Cu—Ag monolith systems that have been tested in an autothermal regime at T>750° C., the starting gas mixture contained hydrogen ($H_2:O_2=2:1$, GHSV=180 000 $h^{-1}$). The catalyst composition is different from that of the present invention and the present invention does not contemplate the use of molecular hydrogen in the feed.

U.S. Pat. No. 4,524,236 issued Jun. 18, 1985 to McCain, assigned to Union Carbide Corporation and U.S. Pat. No. 4,899,003 issued Feb. 6, 1990 to Manyik et al., assigned to Union Carbide Chemicals and Plastics Company Inc. disclose mixed metal oxide catalysts of V—Mo—Nb—Sb. At 375-400° C. the ethane conversion reached 70% with the selectivity close to 71-73%. However, these parameters were achieved only at very low gas hourly space velocities less than 900 $h^{-1}$ (i.e. 720 $h^{-1}$).

U.S. Pat. No. 7,319,179 issued Jan. 15, 2008 to Lopez-Nieto et al., assigned to Consejo Superior de Investigaciones Cientificas and Universidad Politecnica de Valencia, discloses Mo—V—Te—Nb—O oxide catalysts that provided an ethane conversion of 50-70% and selectivity to ethylene up to 95% (at 38% conversion) at 360-400° C. The catalysts have the empirical formula $MoTe_hV_tNb_jA_kO_x$, where A is a fifth modifying element. The catalyst is a calcined mixed oxide (at least of Mo, Te, V and Nb), optionally supported on: (i) silica, alumina and/or titania, preferably silica at 20-70 wt % of the total supported catalyst; or (ii) silicon carbide. The supported catalyst is prepared by conventional methods of precipitation from solutions, drying the precipitate then calcining.

The preparation of a Mo—Te—V—Nb composition is described in WO 2005058498 A1, published Jun. 30, 2005 (corresponding to U.S. published application 2007149390A1). Preparation of the catalyst involves preparing a slurry by combining an inert ceramic carrier with at least one solution comprising ionic species of Mo, V, Te, and Nb, drying the slurry to obtain a particulate product, pre-calcining the dried product at 150-350° C. in an oxygen containing atmosphere and calcining the dried product at 350-750° C. under inert atmosphere. The catalyst prepared exhibits the activity and selectivity in the oxidation reaction comparable to the non-supported catalyst.

A process for preparation of ethylene from gaseous feed comprising ethane and oxygen involving contacting the feed with a mixed oxide catalyst containing vanadium, molybdenum, tantalum and tellurium in a reactor to form effluent of ethylene is disclosed in WO 2006130288 A1, published Dec. 7, 2006, assigned to Celanese Int. Corp. The catalyst has a selectivity for ethylene of 50-80% thereby allowing oxidation of ethane to produce ethylene and acetic acid with high selectivity. The catalyst has the formula $Mo_1V_{0.3}Ta_{0.1}Te_{0.3}O_z$. The catalyst is optionally supported on a support selected from porous silicon dioxide, ignited silicon dioxide, kieselguhr, silica gel, porous and nonporous aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, aluminum silicate, silicon nitride, silicon carbide, and glass, carbon, carbon-fiber, activated carbon, metal-oxide or metal networks and corresponding monoliths; or is encapsulated in a material (preferably silicon dioxide ($SiO_2$), phosphorus pentoxide ($P_2O_5$), magnesium oxide (MgO), chromium trioxide ($Cr_2O_3$), titanium oxide ($TiO_2$), zirconium oxide ($ZrO_2$) or alumina ($Al_2O_3$). However, the methods of preparation of the supported compositions involve the procedures of wet chemistry (solutions are impregnated into the solid support and then the materials are dried and calcined).

U.S. Pat. No. 5,202,517 issued Apr. 13, 1993 to Minet et al., assigned to Medalert Incorporated teaches a ceramic tube for use in the conventional dehydrogenation of ethane to ethylene. The "tube" is a ceramic membrane, the ethane flows inside the tube and hydrogen diffuses out of the tube to improve the reaction kinetics. The reactive ceramic is 5 microns thick on a 1.5 to 2 mm thick support.

U.S. Pat. No. 6,818,189 issued Nov. 16, 2004 to Adris et al., assigned to SABIC teaches in the passage bridging columns 9 and 10 a process in which ceramic pellets are packed around a tubular reactor and different reactants flow around the outside and inside of the tube. The patent is directed to the oxidative dehydrogenation of ethane to ethylene.

There is a significant amount of art on the separation of ethylene and ethane using silver or copper ions in their+1 oxidation state. See U.S. Pat. No. 6,518,476 at Col. 5, lines 10-15 and Col. 16 line 12-Col. 17 line 57. NOVA Chemicals has also disclosed separation of olefins from non-olefins using ionic liquids (dithiolene in CA 2,415,064 (now abandoned)). Also see U.S. Pat. No. 6,120,692 to Exxon; U.S. Pat. No. 6,518,476 issued Feb. 11, 2003 to Union Carbide at columns 16 and 17; the abstract of JP 59172428 published Sep. 29, 1984; and the abstract of JP 59172427 published Sep. 29, 1984.

U.S. Pat. No. 8,107,825 issued Sep. 13, 2011 to Kuznicki et al., assigned to the University of Alberta contains a good outline of prior art for separation of ethane from ethylene and an adsorption method using ETS-10.

U.S. Pat. No. 7,411,107 issued Aug. 12, 2008 to Lucy et al., assigned to BP Chemicals Limited discloses a process for the separation of acetic acid from an oxidative dehydrogenation process to convert ethane to ethylene and acetic acid. The process uses a reversible complex of a metal salt (e.g. Cu or Ag) to separate ethylene (Col. 8). The patent then discloses the acetic acid may be separated from the liquids by a distillation (Col. 13 lines 35 to 40).

United States Patent application 20110245571 in the name of NOVA Chemicals (International) S.A. teaches oxidative dehydrogenation of ethane in a fluidized bed in contact with a bed of regenerative oxides to provide oxygen to the reactor. In this process "free" oxygen is not directly mixed with the feedstock reducing the likelihood of "decompositions".

U.S. Pat. No. 3,904,703 issued Sep. 9, 1975 to Lo et al., assigned to El Paso Products Company teaches a zoned or layered oxidative reactor in which following a zone for oxidative dehydrogenation there is an "oxidation zone" following a dehydrogenation zone to oxidize hydrogen to water. Following the oxidation zone there is an adsorption bed to remove water from the reactants before they enter a subsequent dehydrogenation zone. This is to reduce the impact of water on downstream dehydrogenation catalysts.

United States Patent application 2010/0256432 published Oct. 7, 2010 in the name of Arnold et al., assigned to Lummus discloses at paragraphs 86-94 methods to remove residual oxygen from the product stream. A combustible such as hydrogen or a hydrocarbon may be added to the product stream to eliminate residual oxygen. The patent refers to a catalyst but does not disclose its composition. As noted above it may then be necessary to treat the product stream to eliminate water.

United States Patent application 2004/0010174 (now abandoned) published Jan. 15, 2004 in the name of Wang et al., assigned to ConocoPhillips Company discloses using a circulating fluidized bed (CFB) reactor (similar in design to an FCC reactor) to conduct an oxidative dehydrogenation. The disclosure teaches at paragraph 40 the catalyst acts to carry oxygen into the reactor as lattice oxygen or as adsorbed oxygen. The disclosure teaches away from adding air or oxygen to the feed stream.

U.S. Pat. No. 8,519,210 issued Aug. 27, 2013 to Arnold et al., assigned to Lummus Technology Inc. teaches that the concentration of oxygen in the feed may be limited to, with a margin below, the minimum oxygen for combustion, typically by including steam or inert gases to dilute the feed to below flammability limits.

The present invention seeks to provide a one pass process to oxidatively dehydrogenate lower paraffins (alkanes, preferably n-alkanes) to produce alpha olefins.

DISCLOSURE OF INVENTION

In one embodiment the present invention provides a process for the oxidative dehydrogenation of one or more alkanes selected from the group consisting of ethane and propane and mixtures thereof in the presence of a supported catalyst selected from the group consisting of:

i) catalysts of the formula:

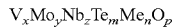

$$V_xMo_yNb_zTe_mMe_nO_p$$

wherein Me is a metal selected from the group consisting of Ta, Ti, W, Hf, Zr, Sb and mixtures thereof; and
x is from 0.1 to 3 provided that when Me is absent x is greater than 0.5;
y is from 0.5 to 1.5;
z is from 0.001 to 3;
m is from 0.001 to 5;
n is from 0 to 2;
and p is a number to satisfy the valence state of the mixed oxide catalyst ii) catalysts of the formula:

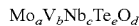

$$Mo_aV_bNb_cTe_eO_d$$

wherein:
a is from 0.75 to 1.25, preferably from 0.90 to 1.10;
b is from 0.1 to 0.5, preferably from 0.25 to 0.4;
c is from 0.1 to 0.5, preferably from 0.1 to 0.35;
e is from 0.1 to 0.35 preferably from 0.1 to 0.3; and
d is a number to satisfy the valence state of the mixed oxide catalyst on a metal oxide support; comprising:

a) passing through an oxidative dehydrogenation reactor containing a fluidized bed of said catalyst said one or more alkanes and oxygen at a temperature from 250° C. to 450° C., a pressure from 3.447 to 689.47 kPa (0.5 to 100 psi) preferably, from 103.4 to 344.73 kPa (15 to 50 psi) and a residence time of said one or more alkanes in said reactor from 0.002 to 10 seconds, and reducing said catalyst, said catalyst having an average residence time in the dehydrogenation reactor of less than 30 seconds;

b) feeding said reduced catalyst to a regeneration reactor and passing a stream of air optionally with additional nitrogen at a temperature from 250° C. to 400° C. and pressures from 3.447 to 689.47 kPa (0.5 to 100 psi) [preferably, from 103.4 to 344.73 kPa (15 to 50 psi) through said bed to oxidize said catalyst; and c) passing said oxidized catalyst back to said oxidative dehydrogenation reactor wherein the amount of oxygen in the feed to said reactor is above the upper flammability limit for said feed. The conversion of alkane to alkene is not less than 50% per pass and the selectivity for the conversion of alkane to alkene is not less than 0.9.

In the further embodiment the process comprises passing the product stream through one or more oxygen scavenging reactors. Preferably, reactors area operated in parallel and one is being oxidized and another is being reduced to lower oxidation state of the metals in the catalyst.

In some embodiments oxygen scavenging reactors use the same catalyst used in oxidative dehydrogenation reactors.

In a further embodiment the oxidative dehydrogenation reactor comprises a riser and the regeneration reactor is a separate fluidized bed reactor, said regeneration reactor being connected with said riser to flow oxidized catalyst back to said riser (e.g. CFB [circulating fluidized bed] type reactor).

In a further embodiment the top of said riser comprises a distributor system to improve temperature control in the reactor [to minimize combustion of the alkane feed and] to maintain the overall selectivity of the reactor above 90%.

A further embodiment comprises passing one or more of low temperature steam and atomized water into said catalyst flow into said riser to cool the catalyst to control the heat balance of the oxidative dehydrogenation reactor.

In a further embodiment there is a downcomer between said oxidative dehydrogenation reactor and said regeneration reactor to flow reduced catalyst from said oxidative dehydrogenation reactor to said regeneration reactor.

A further embodiment comprises passing low temperature steam [counter current to the flow of catalyst through said downcomer] to strip entrained alkane feed and product.

A further embodiment comprises passing air or a mixture of air and nitrogen through the regeneration reactor in an amount to substantially extract the oxygen from the air or a mixture of air and nitrogen and generating a gas product stream comprising not less than 85 vol.-% of nitrogen.

A further embodiment comprises recycling a portion of the oxygen reduced effluent stream from the regenerator reactor and optionally cooling it and recycling it to the regenerator reactor.

In a further embodiment a CO promoter is added to the regenerator reactor.

A further embodiment comprises separating said alkene product from the oxidative dehydrogenation reactor from water in the product stream from the oxidative dehydrogenation unit.

A further embodiment comprises passing unused nitrogen from the effluent stream from the catalyst regeneration reactor to a site integrated unit operation using nitrogen as a part of the feedstock.

In a further embodiment two or more fixed bed reactors are used as scavengers having piping and valves so that the feed to the fluidized bed oxidative dehydrogenation reactor passes through one or more of the fixed bed reactors having an oxidative dehydrogenation which is oxidized to depleted the catalyst of oxygen, and passing the product stream through one or more of the fixed bed reactors having an oxidative dehydrogenation catalyst depleted of oxygen, to remove residual oxygen from the product by reaction and switching the flow of product stream to reactors to oxygen depleted reactors and the flow of feed stream to oxygen rich reactors.

In a further embodiment the site integrated unit operation is selected from an ammonia plant and an acrylonitrile plant, urea plant and, an ammonium nitrate plant.

In a further embodiment the residence time of the catalyst in the oxidative dehydrogenation reactor is less than 30 seconds (preferably less than 10 more desirable less than 5 seconds).

In a further embodiment the residence time of the catalyst in the regeneration reactor is less than 3 minutes.

In a further embodiment the ratio of residence time of the catalyst in the regenerator to the residence time of the catalyst in the oxidative dehydrogenation catalyst is not less than 3.

In a further embodiment the product stream from the oxidative dehydrogenation reactor and at least a portion of the effluent stream from the regenerator reactor are passed through separate steam generators to recover heat.

In a further embodiment the product stream from the oxidative dehydrogenation reactor is cooled and passed through a column to separate combustion products from alkene.

In a further embodiment the product stream from the oxidative dehydrogenation reactor is cooled and passed through an amine unit to remove $CO_2$.

In a further embodiment the support is selected from the group consisting of silicon dioxide, fused silicon dioxide, aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, yttrium oxide.

In a further embodiment the alkane is ethane.
In a further embodiment the catalyst is of the formula:

$$Mo_aV_bNb_cTe_eO_d$$

wherein:
a is from 0.90 to 1.10;
b is from 0.25 to 0.4;
c is from 0.1 to 0.3;
e is from 0.1 to 0.3; and
d is a number to satisfy the valence state of the mixed oxide catalyst on a metal oxide support.

In a further embodiment in the oxidative dehydrogenation reactor the conversion to ethylene is greater than 60%.

In a further embodiment in the oxidative dehydrogenation reactor the selectivity to ethylene is greater than 75%.

BEST MODE FOR CARRYING OUT THE INVENTION

Figure 1:
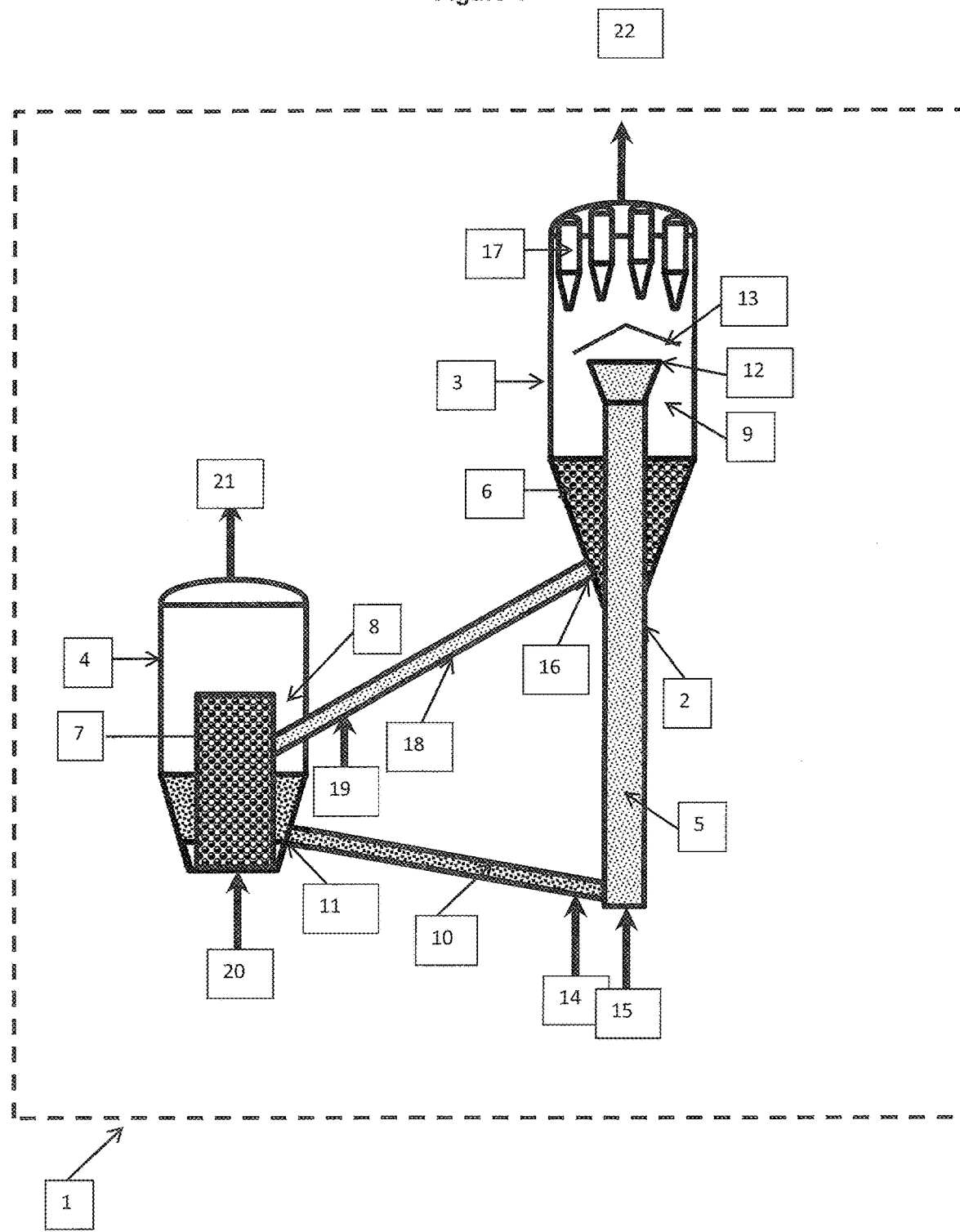
FIG. 1 is a schematic drawing of a CFB reactor useful in accordance with the present invention.

Numbers Ranges:
Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the properties that the present invention desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

All compositional ranges expressed herein are limited in total to and do not exceed 100 percent (volume percent or weight percent) in practice. Where multiple components can be present in a composition, the sum of the maximum amounts of each component can exceed 100 percent, with the understanding that, and as those skilled in the art readily understand, the amounts of the components actually used will conform to the maximum of 100 percent.

Catalysts:
There are a number of catalysts which may be used in accordance with the present invention. The following catalyst systems may be used individually or in combination. One of ordinary skill in the art would understand that combinations should be tested at a laboratory scale to determine if there are any antagonistic effects when catalyst combinations are used.

The oxidative dehydrogenation catalyst of the present invention may be selected from the group consisting of:
i) catalysts of the formula:

$$Ni_xA_aB_bD_dO_e$$

wherein
x is a number from 0.1 to 0.9 preferably from 0.3 to 0.9, most preferably from 0.5 to 0.85, most preferably 0.6 to 0.8;
a is a number from 0.04 to 0.9;
b is a number from 0 to 0.5;
d is a number from 0 to 0.0.5;
e is a number to satisfy the valence state of the catalyst;
A is selected from the group consisting of Ti, Ta, V, Nb, Hf, W, Y, Zn, Zr, Si and Al or mixtures thereof;

B is selected from the group consisting of La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg and mixtures thereof;
D is selected from the group consisting of Ca, K, Mg, Li, Na, Sr, Ba, Cs, and Rb and mixtures thereof; and
O is oxygen; and
ii) catalysts of the formula:

$$Mo_f X_g Y_h$$

wherein
X is selected from the group consisting of Ba, Ca, Cr, Mn, Nb, Ta, Ti, Te, V, W and mixtures thereof;
Y is selected from the group consisting of Bi, Ce, Co, Cu, Fe, K, Mg V, Ni, P, Pb, Sb, Si, Sn, Ti, U and mixtures thereof;
f=1;
g is 0 to 2;
h is 0 to 2, with the proviso that the total value of h for Co, Ni, Fe and mixtures thereof is less than 0.5;
and catalysts of formula iii) below,
and mixtures thereof.

In one embodiment the catalyst is the catalyst of formula i) wherein x is from 0.5 to 0.85, a is from 0.15 to 0.5, b is from 0 to 0.1 and d is from 0 to 0.1. In catalyst i) typically A is selected from the group consisting of Ti, Ta, V, Nb, Hf, W, Zr, Si, Al and mixtures thereof, B is selected from the group consisting of La, Ce, Nd, Sb, Sn, Bi, Pb, Cr, Mn, Mo, Fe, Co, Cu, Ru, Rh, Pd, Pt, Ag, Cd, Os, Ir and mixtures thereof and D is selected from the group consisting of Ca, K, Mg, Li, Na, Ba, Cs, Rb and mixtures thereof.

In an alternative embodiment the catalyst is catalyst ii). In some embodiments of this aspect of the invention typically X is selected from the group consisting of Ba, Ca, Cr, Mn, Nb, Ti, Te, V, W and mixtures thereof, Y is selected from the group consisting of Bi, Ce, Co, Cu, Fe, K, Mg V, Ni, P, Pb, Sb, Sn, Ti and mixtures thereof.

One additional particularly useful family of catalysts iii) comprise one or more catalysts selected from the group consisting of a mixed oxide catalyst of the formula:

$$V_x Mo_y Nb_z Te_m Me_n O_p,$$

wherein Me is a metal selected from the group consisting of Ti, Ta, Sb, Hf, W, Y, Zn, Zr, La, Ce, Pr, Nd, Sm, Sn, Bi, Pb Cr, Mn, Fe, Co, Cu, Ru, Rh, Pd, Pt, Ag, Cd, Os, Ir, Au, and mixtures thereof; and
x is from 0.1 to 3, preferably from 0.5 to 2.0 most preferably from 0.75 to 1.5 and provided that when Me is absent x is greater than 0.5;
y is from 0.5 to 1.5, preferably from 0.75 to 1.0;
z is from 0.001 to 3, preferably from 0.1 to 2, most preferably from 0.5 to 1.5;
m is from 0.001 to 5, preferably from 1 to 4;
n is from 0 to 2, preferably n is 0, however when Me is present n is preferably from 0.5; to 1.5; and
p is a number to satisfy the valence state of the mixed oxide catalyst.

In one embodiment the catalyst has the formula:

$$Mo_a V_b Nb_c Te_e O_d$$

wherein:
a is from 0.90 to 1.10, preferably 0.95 to 1.1;
b is from 0.25 to 0.4, preferably 0.3 to 0.35;
c is from 0.1 to 0.3, preferably 0.1 to 0.15;
e is from 0.1 to 0.3, preferably 0.1 to 0.25; and
d is a number to satisfy the valence state of the mixed oxide catalyst on a metal oxide support.

In a further embodiment in the catalyst the ratio of x:m is from 0.3 to 10, most preferably from 0.5 to 8, desirably from 0.5 to 6.

The methods of preparing the catalysts are known to those skilled in the art.

For example, the catalyst may be prepared by mixing aqueous solutions of soluble metal compounds such as hydroxides, sulphates, nitrates, halides, salts of lower ($C_{1-5}$) mono or di carboxylic acids and ammonium salts or the metal acid per se. For instance, the catalyst could be prepared by blending solutions such as ammonium metavanadate, niobium oxalate, ammonium molybdate, telluric acid, etc. The resulting solution is then dried typically in air at 100-150° C. and calcined in a flow of inert gas such as those selected from the group consisting of $N_2$, He, Ar, Ne and mixtures thereof at 200-600° C., preferably at 300-500° C. The calcining step may take from 1 to 20, typically from 5 to 15 usually about 10 hours. The resulting oxide is a friable solid typically insoluble in water.

The Support/Binder:

There are several ways the oxidative dehydrogenation catalyst may be supported or bound.

Preferred components for forming ceramic supports and for binders include oxides of titanium, zirconium, aluminum, magnesium, silicon, phosphates, boron phosphate, zirconium phosphate and mixtures thereof, for both fluidized and fixed bed reactors. In the fluidized bed typically catalyst is generally spray dried with the binder, typically forming spherical particles ranging in size (effective diameter) from 40-100 urn. However, one needs to be careful to insure that particles area sufficiently robust to minimize the attrition in the fluidized bed.

The support for the catalyst for the fixed bed may further be ceramic precursor formed from oxides, dioxides, nitrides, carbides selected from the group consisting of silicon dioxide, fused silicon dioxide, aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, yttrium oxide, aluminum silicate, silicon nitride, silicon carbide and mixtures thereof.

In one embodiment the support for the fixed bed may have a low surface area less than 20 $m^2/g$, alternatively, less than 15 $m^2/g$, alternatively, less than 3.0 $m^2/g$ for the oxidative dehydrogenation catalyst. Such support may be prepared by compression molding. At higher pressures the interstices within the ceramic precursor being compressed collapse. Depending on the pressure exerted on the support precursor the surface area of the support may be from about 20 to 10 $m^2/g$.

The low surface area support could be of any conventional shape such as spheres, rings, saddles, etc.

In the present invention the oxidized catalyst in the fluidized bed contains one or more of lattice oxygen and adsorbed oxygen. The supported catalyst together with added air or preferably oxygen passes together through an oxidative dehydrogenation reactor, and the catalyst is reduced when ethane is converted to ethylene. Then the supported catalyst is passed by the downcomer to the regeneration reactor where it is oxidized.

It is important that the support be dried prior to use (i.e. before adding catalyst). Generally, the support may be heated at a temperature of at least 200° C. for up to 24 hours, typically at a temperature from 500° C. to 800° C. for about 2 to 20 hours, preferably 4 to 10 hours. The resulting support will be free of adsorbed water and should have a surface hydroxyl content from about 0.1 to 5 mmol/g of support, preferably from 0.5 to 3 mmol/g.

The amount of the hydroxyl groups on silica may be determined according to the method disclosed by J. B. Peri and A. L. Hensley, Jr., in J. Phys. Chem., 72 (8), 2926, 1968, the entire contents of which are incorporated herein by reference.

The dried support for the fixed bed catalyst may then be compressed into the required shape by compression molding. Depending on the particle size of the support, it may be combined with an inert binder to hold the shape of the compressed part.

Loadings:

Typically the catalyst loading on the support for the fixed bed catalyst provides from 1 to 30 weight % typically from 5 to 20 weight %, preferably from 8 to 15 weight % of said catalyst and from 99 to 70 weight %, typically from 80 to 95 weight %, preferably from 85 to 92 weight %, respectively, of said support.

The catalyst may be added to the support in any number of ways. For example the catalyst could be deposited from an aqueous slurry onto one of the surfaces of the low surface area support by impregnation, wash-coating, brushing or spraying. The catalyst could also be co-precipitated from a slurry with the ceramic precursor (e.g. alumina) to form the low surface area supported catalyst.

The catalyst loading for the fluidized bed may be chosen based on a number of factors including the volume of bed, the flow rate of alkane through the bed, energy balance in the bed, binder type, etc. For the fluidized bed catalyst loading may cover a wide range of values ranging from 10 wt.-% up to 90 wt.-%, typically above 20 wt.-% desirably above 35 wt.-%.

In the present invention the feed to the oxidative dehydrogenation reactor includes oxygen in an amount above the upper explosive/ignition limit. For example for ethane oxidative dehydrogenation, typically the oxygen will be present in an amount of not less than about 5 mole-% preferably about 18 mole-%, for example from about 22 to 27 mole-%, or 23 to 26 mole-%. It is desirable not to have too great an excess of oxygen as this may reduce selectivity arising from combustion of feed or final products. Additionally too high an excess of oxygen in the feed stream may require additional separation steps at the downstream end of the reaction.

The process of the present invention will be described in conjunction with FIG. 1 which schematically illustrates a circulating fluidized bed reactor.

In one embodiment the reactor system 1 comprises a fluidized bed oxidative dehydrogenation reactor 3 and a regenerator reactor 4. The fluidized bed oxidative dehydrogenation reactor riser 2 and the regeneration reactor 4 are joined by a downcomer 10 which conducts clean oxidized supported catalyst from the regenerator reactor 4 to the oxidative dehydrogenation reactor riser 2. Each of the fluidized bed oxidative dehydrogenation reactor riser 2, the fluidized bed 6 in the dehydrogenation reactor 3 and the regeneration reactor 4 contain fluidized bed of catalyst particles 5, 6 and 7 respectively. In the oxidative dehydrogenation reactor riser 2 and the regeneration reactor 4 above fluidized catalyst beds 5 and 7 are disengagement zones 8 and 9, respectively.

The inlet 11 to downcommer 10 is attached to the regenerator reactor 4 generally at a point between about ⅓ to ⅔ the height of the fluidized bed 7. The downcommer 10 enters the bottom of the oxidative dehydrogenation reactor riser 2. The reactor riser 2 extends up into the dehydrogenation reactor 3 above the fluid level of the fluidized bed 6 (typically ⅓ to ⅔ of height). The reactor riser 2, flares to form an inverted cone disperser 12 to provide a disengagement zone for catalyst from the product. Optionally, a disperser plate 13 may be used above the cone 12. The disperser may have a shape other than an inverted cone; however, care must be taken to ensure a substantially uniform gas flow around the disperser.

The oxidative dehydrogenation reactor operates at temperatures below 450° C. typically from 350° to 450°, pressures from 3.447 to 689.47 kPa (0.5 to 100 psi) preferably, from 103.4 to 344.73 kPa (15 to 50 psi) and a residence time of the one or more alkanes in the oxidative dehydrogenation reactor riser 2 from 0.002 to 20 seconds.

Flared section 12 of the riser should be sufficiently broad to cause the catalyst particles to drop in the fluidized bed zone 6, the disperser plate 13 should be high enough to minimize catalyst attrition.

Port 14 in the riser 10 permits the introduction of one or more of low temperature steam and atomize water (e.g. a mist), at a temperature at least about 25° C. desirably 50° C. lower than the temperature of the oxidative dehydrogenation reactor. In some embodiments steam has a temperature from about 200° C. to about 400° C., in further embodiments the temperature may be from about 300° C. to 350° C. The steam cools the catalyst coming from the regenerator reactor 4 and also removes any entrained or absorbed impurities (e.g. ethylene or air). The atomized water may have temperature from 50° C. to 75° C. on introduction to port 14. All or part of the atomized water can be recycled water from the reaction product.

Port 15 at or towards the base of the oxidative dehydrogenation reactor riser 2 is an inlet for the hydrocarbon feed typically high purity ethane mixed with oxygen or an oxygen containing gas. The hydrocarbon feed and oxygen could be combined proximate and upstream of the oxidative dehydrogenation reactor. As this is a fluidized bed reactor it is necessary that the upward flow of hydrocarbon feed and oxygen containing gas be sufficiently well distributed to fluidize the bed of catalyst particles to minimize hot spots.

The process of the present invention may be used to generate ethylene from relatively pure feedstock.

The ethane individually should comprise about 95 wt.-% of ethane, preferably 98 wt.-% of ethane and not more than about 5 wt.-% of associated hydrocarbons such as methane. Preferably the feed is oxygen having a relatively high purity in some embodiments above 90% pure, in further embodiments greater than 95% pure. While air may be used as a source for oxygen it may give rise to downstream separation issues.

In the further embodiment of the invention the reactor of the present invention may be used to replace an ethane/ethylene splitter or off-gas from refinery or other hydrocarbon processing process in which case the feedstock can comprise from 10-80 vol.-% ethylene and balance ethane.

To maintain a viable fluidized bed, the mass gas flow rate through the bed must be above the minimum flow required for fluidization, and preferably from about 1.5 to about 10 times $U_{mf}$ and more preferably from about 2 to about 6 times $U_{mf}$. $U_{mf}$ is used in the accepted form as the abbreviation for the minimum mass gas flow required to achieve fluidization, C. Y. Wen and Y. H. Yu, "Mechanics of Fluidization", Chemical Engineering Progress Symposium Series, Vol. 62, p. 100-111 (1966). Typically the superficial gas velocity required ranges from 0.3 to 5 m/s.

At the upper end of the oxidative dehydrogenation reactor, below disengagement zone 9 is port 16 which permits the spent catalyst stream to settle and leave the reactor. At the top of the reactor 3, there are cyclones 17 to remove any catalyst fines, which were not settled in disengagement zone 9.

The average residence time of the supported catalyst in the oxidative dehydrogenation reactor riser 2 is less than about 30 seconds in some cases less than 15 seconds in some cases from 1 to 6 seconds. The port 16 connects downcomer 18 with the oxidative dehydrogenation reactor 3 and the regeneration reactor 4. Port 19 in the downcomer 18 is positioned proximate the regeneration reactor 4. Port 19 allows the introduction of steam at a temperature from about 300° C. to 500° C., in some embodiments from 350° C. to 450° C. to flow counter current to the stream of spent catalyst to remove entrained feedstock and product. In some cases the steam may also burn of surface coke on the catalyst particles. The flow rate of the steam in the downcomer should be sufficiently low to prevent the supported catalyst from being pushed back into disengagement zone 9.

The regeneration reactor is also a fluidized bed reactor. Port 20 at the bottom of the regeneration reactor permits air and in some cases recycled cooled nitrogen back into the reactor. The regeneration reactor is typically operated at temperatures from 250° C. to 400° C. and pressures from 3.447 to 689.47 kPa (0.5 to 100 psi), preferably, from 103.4 to 344.73 kPa (15 to 50 psi). The residence time of the supported catalyst in the regeneration reactor is less than 3 minutes. Typically the ratio of the residence time of the catalyst in the regenerator reactor to the residence time in the oxidative dehydrogenation reactor is not less than 3.

Port 21 on the upper portion of the regenerator reactor 4, above the fluidized bed of supported catalyst particles permits the off gas to leave the reactor. There may be cyclones as described for the oxidative dehydrogenation reactor 3 in the upper section of the regenerator reactor 4 to remove any catalyst fines from nitrogen product stream. Air and optionally nitrogen which may be cooled are passed through the regeneration reactor. The oxygen is substantially taken from the air. The off gas will comprise from 85 to 100% of nitrogen.

The above description of the circulating fluidized bed reactor has been largely schematic. There may be various valves, filters, etc. at the ports. The selection of appropriate valves would be well known to those skilled in the art. Similarly there may be suitable fans and compression means used to force gases through the system. The selection of appropriate fans or compressors or expanders for cooling would be known to one of ordinary skill in the art.

It is desirable to recover as much energy as possible from the oxidative dehydrogenation reaction and the regeneration reaction. The ethylene feed and the co-products (e.g. $CO_2$ and CO) from the oxidative reactor are fed to separate steam generators to generate steam. Part of the steam may be recycled back to the process. The steam could be injected in the riser to cool the catalyst particles. The steam could also be injected into the downcomer to burn off any coke and to entrain any absorbed or adsorbed feed or products.

The oxygen containing stream passing through the regenerator is substantially depleted of oxygen on exit from the reactor (e.g. the exit stream comprises not less than about 90% of nitrogen). If nitrogen is also used as a component of the feed stream a part of the product stream may be recycled to the inlet for the regeneration reactor. The portion of the product stream from the regeneration reactor may be subject to one or more cooling or refrigeration steps to maintain the heat balance in the regenerator. In some embodiments a CO promoter may be added to the regenerator to minimize the heat release in regenerator (i.e. reduce/control $CO_2$ production).

There are a number of patents and application which teach CO promoters including the following.

U.S. Pat. No. 4,064,039 issued Dec. 20, 1977 to Penick, assigned to Mobil Oil Corporation teaches adding up to 50, typically from 0.01 to 1 ppm of Platinum group metals and rhenium to promote CO combustion.

U.S. Pat. No. 4,072,600 issued Feb. 7, 1978 to Schwartz, assigned to Mobil Oil Corporation teaches adding 1 to 50 ppm of a metal selected from the group consisting of platinum, palladium, iridium, osmium, ruthenium and rhenium and mixtures to promote CO combustion.

U.S. Pat. No. 4,093,535 issued Jun. 6, 1978 to Schwartz, assigned to Mobil Oil Corporation teaches adding 1 to 50 ppm of a metal selected from the group consisting of platinum, palladium, iridium, osmium, ruthenium and rhenium and mixtures to promote CO combustion.

U.S. Pat. No. 5,565,399 issued Oct. 15, 1996 to Fraenkel et al., assigned to Engelhard Corporation teaches supports for CO promoters comprising alumina microspheres having been impregnated with at least 2 weight percent $La_2O_3$ and from 3 to 8 weight percent $CeO_2$, which microspheres are substantially free from alpha alumina and having an x-ray pattern showing the presence of crystalline $CeO_2$.

The process of the present invention should be operated to have a conversion of not less than 80% (to ethylene) and a selectivity of not less than 90%, preferably greater than 95% to ethylene.

Separation of Product Streams:

The stream 22 exiting the dehydrogenation reaction comprises ethylene, water (vapour-steam) and a small amounts of ethane, unconsumed oxygen and off gases typically CO and $CO_2$. The issue of separation needs to be considered in the context of the intended use for the ethylene.

There are a number of processes which may use dilute ethylene such as polymerization processes. However, this approach needs to be balanced with the effect of polar molecules such as CO and $CO_2$ and oxygen on the catalyst used for the polymerization. It may be preferable to separate the polar molecules prior to separation of ethylene and ethane. The polar molecules may be separated by an adsorption bed such as a zeolite bed. In the simplest embodiment, depending on the ratios of the components the bed could be regenerated and all the components fed to a burner to burn the CO. However, at a chemical complex there are other unit operations which could use CO as a feed (various carboxylic acid and anhydride processes (acetic acid, meth acrylic acid and maleic anhydride). If there is a significant amount of CO and $CO_2$ the components could be separated. There are a number of well-known methods in the art to separate $CO_2$ and CO. The stream would be cooled and washed and then passed through an adsorber such as activated carbon (to remove impurities from the $CO_2$) or a liquid amine separator or a liquid carbonate separator to absorb the $CO_2$. CO could be separated by a number of techniques. Depending on the volume a vacuum separation method using activated carbon as an adsorbent may be suitable, a membrane separation may be suitable and adsorption on copper ions (on a suitable support) may be suitable.

Oxygen Removal—Fixed Bed:

In one embodiment there may be two or more fixed bed reactors having an oxidative dehydrogenation catalyst which releases or takes up oxygen are used as scavengers to accommodate the product flow out of the circulating fluidized bed oxidative dehydrogenation reactor. The fixed bed reactors have piping and valves so that the feed to the fluidized bed oxidative dehydrogenation reactor passes through one or more of the fixed bed reactors having a catalyst containing oxygen which is consumed or given up. This is not so much of an issue with the pre-reactor operating in oxidative dehydrogenation mode since any excess alkane not dehydrogenated in the pre-reactor will be converted in the fluidized bed oxidative dehydrogenation reactor. The key issue is depleting the catalyst in the fixed bed reactor of oxygen. The piping and valves flow the product stream through one or more of the fixed bed reactors having oxidative dehydrogenation catalysts which are depleted of oxygen. The depleted fixed bed catalyst scavenges oxygen from the product stream. As noted the valves and piping of the streams can be operated so that feed streams flow through the oxygenated fixed bed catalyst reactor and the product stream flows through one or more of the oxygen depleted fixed beds catalyst reactors.

The oxidative dehydrogenation catalyst containing oxygen may have oxygen as lattice oxygen, adsorbed oxygen or adsorbed oxygen on the catalyst, the support or both. The oxidative dehydrogenation catalyst depleted of oxygen has a reduced, preferably, about 60% less oxygen in the catalyst and support as lattice oxygen, adsorbed oxygen or adsorbed oxygen on the catalyst, the support or both.

Preferably, at the exit of the fluidized bed oxidative dehydrogenation reactor is an oxygen sensor. Additionally, there should be an oxygen sensor at the exit for the dehydrogenated product from each fixed bed reactor to determine the oxygen level leaving the product leaving that fixed bed reactor. When the oxygen level rises at the dehydrogenated product outlet of the fixed bed reactor operating in scavenger mode it indicates the catalyst have substantially taken up reactive oxygen (and may be returned to use as a pre-reactor). The amount of reactive oxygen uptake by the oxygen depleted catalyst in the pre-reactor operation in oxygen scavenging or chemisorption mode should be not less than about 1.5%, typically about 2% of the total oxygen in the catalyst (this will also correspond to the amount of reactive oxygen available for release from the catalyst in the pre-reactors in oxidative dehydrogenation mode).

Figure 10:
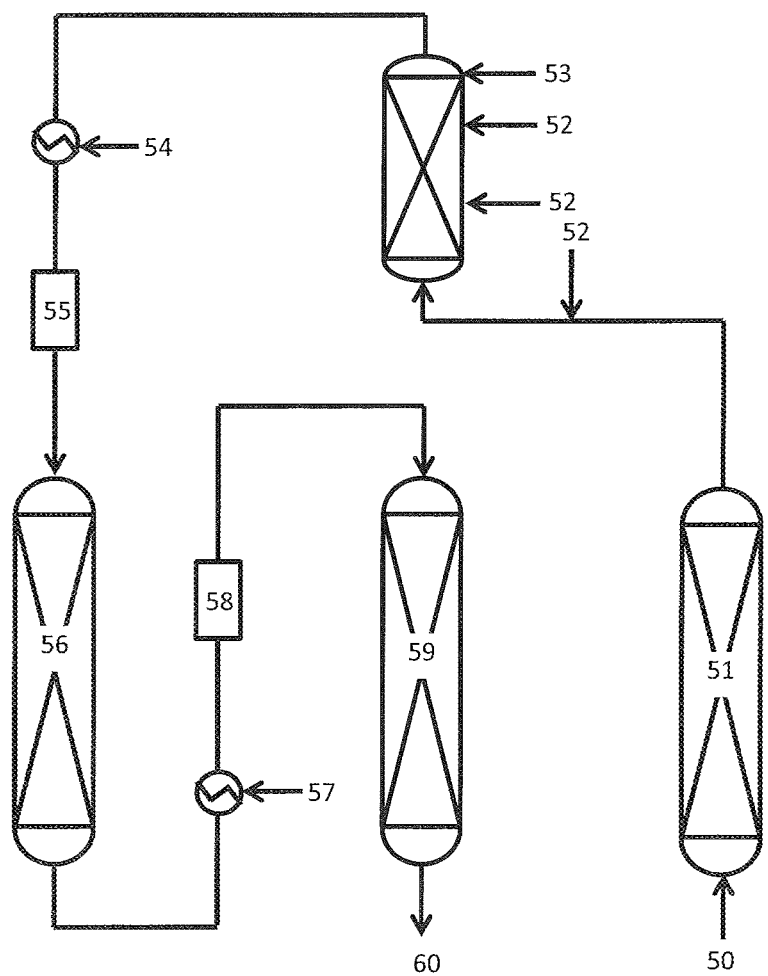
FIGS. 10, 11, and 12 illustrate how a series of three fixed bed catalysts may be used to scavenge oxygen from the product stream in an oxidative dehydrogenation reactor.
Figure 11:
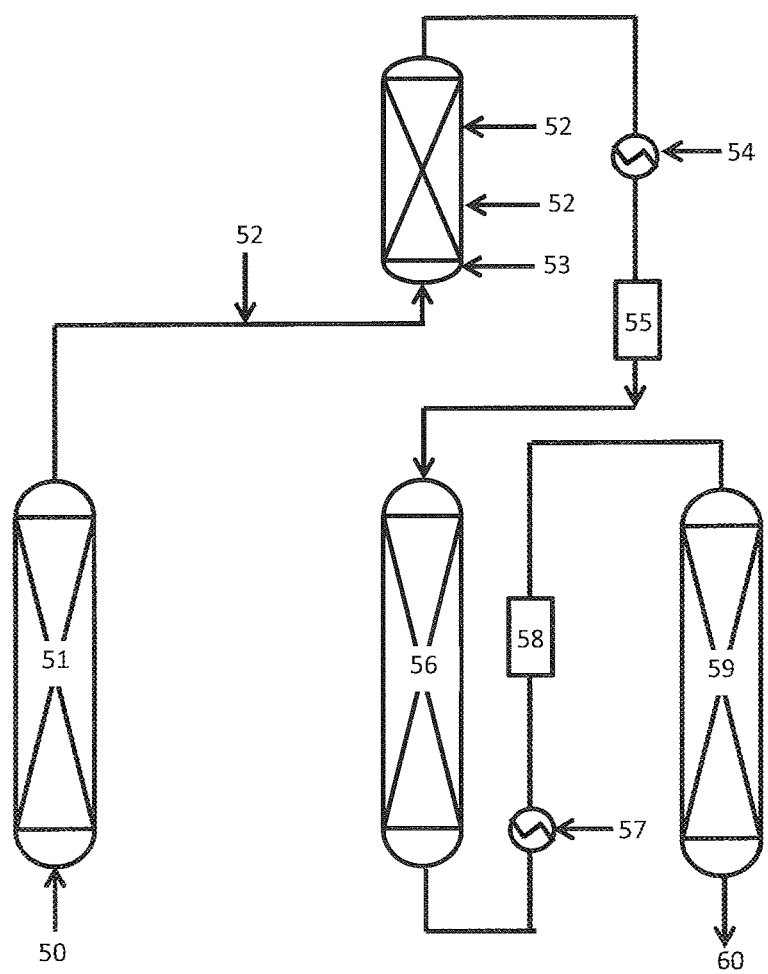
Figure 12:
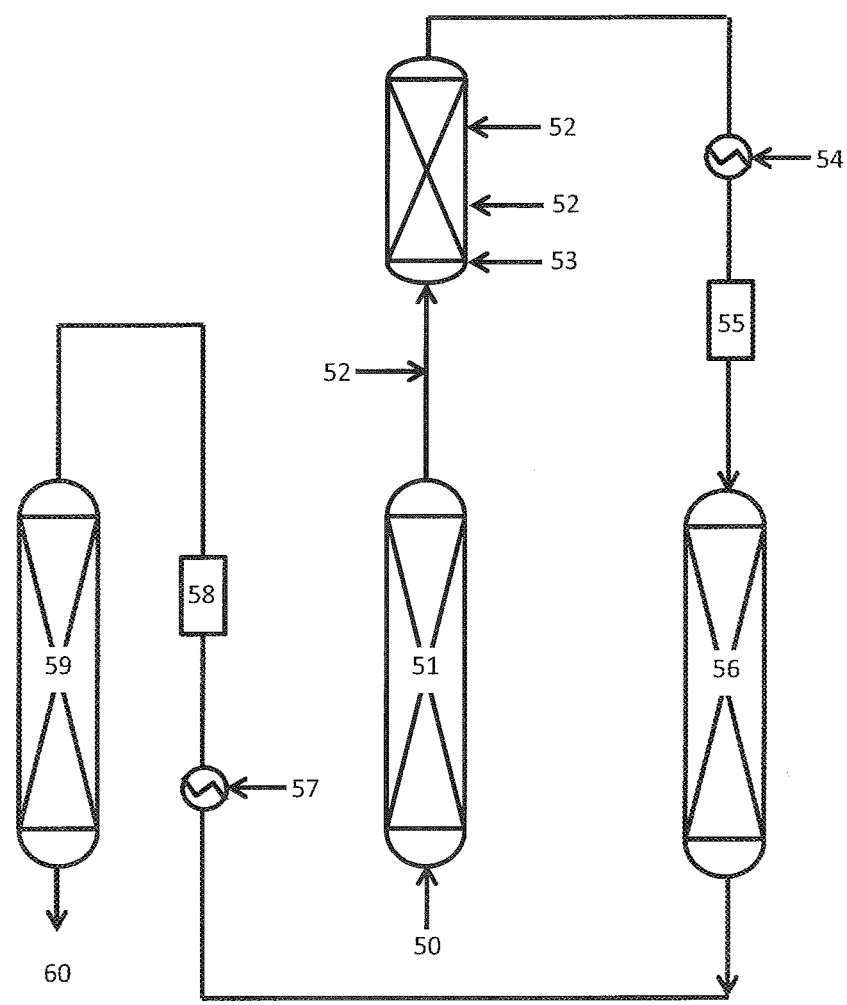

One mode for operation using three pre-reactors is illustrated schematically in FIGS. 10, 11, and 12 (in which like parts have like numbers) and the table below. In FIGS. 10, 11, and 12 the valves are not shown. The main reactor configuration is the same however the switching of the valves causes the pre-reactor, scavenger reactor and the guard reactor to appear to "switch" places. One pre-reactor operates as such and converts part of the feed stream to ethylene. One oxygen depleted pre-reactor acts as a primary oxygen scavenger or chemisorption reactor and a second pre-reactor (also oxygen depleted acts as a guard or secondary oxygen scavenger or chemisorption reactor).

Operation:

| Process Step | Process streams flow sequence |
|---|---|
| Step 1 (FIG. 10): | Ethane (50) is routed to a fixed bed reactor (51) (preferably oxygen saturated). Some of the ethane is converted to ethylene and the product together with oxygen (52) is routed to the fluidized bed oxidative dehydrogenation reactor (53), where most or all ethane is converted to ethylene. The product is cooled in a condenser (54) to a temperature from 50° C. to 270° C., and optionally water is knocked out of the product stream in knock out drum (55) (adsorbed by one or more guard beds). The cooled product stream is routed to a primary scavenging oxygen depleted fixed bed reactor which acts as a lead oxygen scavenger reactor (56). Oxygen scavenging/chemisorption is exothermic, the product stream from the primary oxygen scavenging reactor may be cooled in a condenser (57) and routed through water knock out drum (58) to the secondary or guard oxygen scavenger fixed bed reactor (59) (oxygen depleted pre-reactor) - (cooling down may not be required, since the only reason for cooling is to reduce any oxidation reaction of the final product (60) (e.g. production of CO and $CO_2$ or both), in the secondary or guard oxygen depleted pre-reactor initially there is a very low level of reactive oxygen (typically less 50, preferably less than 25, most preferably less than 10 ppm of reactive oxygen in the feed stream) will be present; A slightly elevated temperature (2° C. to 5° C. higher) will help to remove it to very low level without converting the product to CO and $CO_2$. Oxygen sensors, not shown, are active on inlets to the lead (primary) and fixed bed oxygen scavenging guard reactor (secondary oxygen scavengers and the outlet of the guard scavenger. The operation is to go to step 2 when the oxygen content in the product stream exiting the guard reactor exceeds specified value. |
| Step 2: (FIG. 11) | Changes from Step 1 (FIG. 10): The former fixed bed oxidative dehydrogenation reactor (pre-reactor) (51) now becomes guard scavenger (59); former guard scavenger (59) now becomes lead scavenger (56), former lead scavenger (56) becomes pre-reactor (51). Operation is the same as described for the Step 1. |

| Process Step | Process streams flow sequence |
|---|---|
| Step 3: (FIG. 12) | Changes from Step 2 (FIG. 11): Fixed bed oxidative dehydrogenation reactor (Pre-reactor (51) becomes guard scavenger reactor (59); former guard scavenger becomes lead scavenger reactor (56,) and former lead scavenger becomes the pre-reactor (51). Operation is the same as described for the Step 1. |
| Step 4: (FIG. 10) | Return to Step 1. |

In an alternate embodiment the oxygen may be separated from the product stream using cryogenic methods. However, this adds both capital and operating costs to the process.

The above scavenging process is more fully described in Canadian Patent application 2,833,822 filed Nov. 21, 2013, the text of which is herein incorporated by reference.

Residual gases from the downcomer would also be subject to the same separation techniques to recover them.

As noted above it may not be necessary to separate the ethane from the ethylene at this stage however, if desired there are a number of techniques that may be used.

The most common techniques would be to use a cryogenic C2 splitter. Other separation techniques include the following.

One method of separation of the product stream is by absorption. The gaseous product stream comprising primarily ethane and ethylene may be contacted in a counter current flow with a heavier paraffinic oil such as mineral seal oil or medicinal white oil at a pressure up to 800 psi (about $5.5 \times 10^3$ kPa) and at temperatures from about 25° F. to 125° F. (about −4° C. to about 52° C.). The ethylene and lower boiling components are not absorbed into the oil. The ethane and higher boiling components are absorbed into the oil. The ethylene and lower boiling components may then be passed to the C2 splitter if required. The absorption oil may be selectively extracted with a solvent such as furfural, dimethyl formamide, sulfur dioxide, aniline, nitrobenzene, and other known solvents to extract any heavier paraffins. This process is more fully described in U.S. Pat. No. 2,395,362 issued May 15, 1945 to Welling, assigned to Phillips Petroleum Company, the contents of which are herein incorporated by reference.

Another separation method is an adsorption method. The adsorbent preferentially adsorbs one of the components in the product stream. The adsorption method typically comprises a train of two or more adsorption units so that when a unit has reached capacity the feed is directed to an alternate unit while the fully loaded unit is regenerated typically by one or more of a change in temperature or pressure or both.

There is a significant amount of art on the separation of ethylene and ethane using silver or copper ions in their+1 oxidation state. The olefins are preferentially absorbed into a complexing solution that contains the complexing agent selected from silver (I) or copper (I) salts dissolved in a solvent. Some silver absorbents include silver nitrate, silver fluoroborate, silver fluorosilicate, silver hydroxyfluoroborate, and silver trifluoroacetate. Some copper absorbents include cuprous nitrate; cuprous halides such as cuprous chloride; cuprous sulfate; cuprous sulfonate; cuprous carboxylates; cuprous salts of fluorocarboxylic acids, such as cuprous trifluoroacetate and cuprous perfluoroacetate; cuprous fluorinated acetylacetonate; cuprous hexafluoroacetylacetonate; cuprous dodecylbenzenesulfonate; copper-aluminum halides, such as cuprous aluminum tetrachloride; $CuAlCH_3C_{13}$; $CuAlC_2H_5Cl_3$; and cuprous aluminum cyanotrichloride. If the product stream has been dried prior to contact with the liquid adsorbent, the absorbent should be stable to hydrolysis. The complexing agent preferably is stable and has high solubility in the solvent. After one adsorbent solution is substantially loaded the feed of product stream is switched to a further solution. The solution of adsorbent which is fully loaded is then regenerated through heat or pressure changes or both. This releases the ethylene.

These types of processes are described in U.S. Pat. No. 6,581,476 issued Feb. 11, 2003 to Culp et al., assigned to Union Carbide Chemicals & Plastics Corporation and U.S. Pat. No. 5,859,304 issued Jan. 12, 1999 to Barchas et al., assigned to Stone and Webster Engineering the contents of which are herein incorporated by reference.

In an alternative to the solution process supports such as zeolite 4A, zeolite X, zeolite Y, alumina and silica, may be treated with a copper salt, to selectively remove carbon monoxide and/or olefins from a gaseous mixture containing saturated hydrocarbons (i.e. paraffins) such as ethane and propane. U.S. Pat. No. 4,917,711 issued Apr. 17, 1990 to Xie et al., assigned to Peking University describes the use of such supported adsorbents, the contents of which are incorporated herein by reference.

Similarly, U.S. Pat. No. 6,867,166 issued Mar. 15, 2005 and U.S. Pat. No. 6,423,881 and Jul. 23, 2002 to Yang et al., assigned to the Regents of the University of Michigan, which are herein incorporated by reference, describe the use of copper salts and silver compounds supported alternatively on silica, alumina, MCM-41 zeolite, 4A zeolite, carbon molecular sieves, polymers such as Amberlyst-35 resin, and alumina to selectively adsorb olefins from gaseous mixtures containing olefins and paraffins. Both kinetic and thermodynamic separation behavior was observed and modeled. The adsorption of the olefin takes place at pressures from 1 to 35 atmospheres, preferably less than 10 atmospheres, most preferably less than 2 atmospheres at temperatures from 0 to 50° C., preferably from 25 to 50° C. and the desorption occurs at pressures from 0.01 to 5 atmospheres, preferably 0.1 to 0.5 at temperatures from 70° C. to 200° C., preferably from 100° C. to 120° C.

In a further embodiment the adsorbent may be a physical adsorbent selected from the group consisting of natural and synthetic zeolites without a silver or copper salt.

In general, the adsorbent may be alumina, silica, zeolites, carbon molecular sieves, etc. Typical adsorbents include alumina, silica gel, carbon molecular sieves, zeolites, such as type A and type X zeolite, type Y zeolite, etc. The preferred adsorbents are type A zeolites, and the most preferred adsorbent is type 4A zeolite.

Type 4A zeolite, i.e. the sodium form of type A zeolite, has an apparent pore size of about 3.6 to 4 Angstrom units. This adsorbent provides enhanced selectivity and capacity in adsorbing ethylene from ethylene-ethane mixtures and propylene from propylene-propane mixtures at elevated temperatures. This adsorbent is most effective for use in the invention when it is substantially unmodified, i.e. when it has only sodium ions as its exchangeable cations. However, certain properties of the adsorbent, such as thermal and light stability, may be improved by partly exchanging some of the sodium ions with other cations (other than silver or copper). Accordingly, it is within the scope of the preferred embodiment of the invention to use a type 4A zeolite in which some of the sodium ions attached to the adsorbent are replaced with other metal ions, provided that the percentage of ions exchanged is not so great that the adsorbent loses its type 4A character. Among the properties that define type 4A character are the ability of the adsorbent to selectively adsorb ethylene from ethylene-ethane mixtures and propylene from propylene-propane gas mixtures at elevated temperatures, and to accomplish this result without causing significant oligomerization or polymerization of the alkenes present in the mixtures. In general, it has been determined that up to about 25 percent (on an equivalent basis) of the sodium ions in 4A zeolite can be replaced by ion exchange with other cations without divesting the adsorbent of its type 4A character. Cations that may be ion exchanged with the 4A zeolite used in the alkene-alkane separation include, among others, potassium, calcium, magnesium, strontium, zinc, cobalt, manganese, cadmium, aluminum, cerium, etc. When exchanging other cations for sodium ions it is preferred that less than about 10 percent of the sodium ions (on an equivalent basis) be replaced with such other cations. The replacement of sodium ions may modify the properties of the adsorbent. For example, substituting some of the sodium ions with other cations may improve the stability of the adsorbent. As disclosed in U.S. Pat. No. 5,744,687 issued Apr. 28, 1998 to Ramachandran et al., assigned to the BOC Group, Inc. the contents of which are herein incorporated by reference.

A particularly preferred zeolite is ZSM-5.

In addition to zeolites there are a number of titanosilicate homologues referred to as ETS compounds.

U.S. Pat. No. 5,011,591 discloses the synthesis of a large pore diameter titanosilicate designated "ETS-10". In contrast to ETS-4 and CTS-1 (referenced below), the large pore titanosilicate material, ETS-10, which has pore diameters of about 8 Å, cannot kinetically distinguish light olefins from paraffins of the same carbon number. Nevertheless, high degrees of selectivity have been reported for the separation of ethylene from ethane using as prepared ETS-10 zeolites; see: Al-Baghli and Loughlin in *J. Chem. Eng. Data* 2006, v51, p 248. The authors demonstrate that Na-ETS-10 is capable of selectively adsorbing ethylene from a mixture of ethylene and ethane under thermodynamic conditions, even at ambient temperature. Although, the reported selectivity for ethylene adsorption using Na-ETS-10 was high at ambient temperature, the adsorption isotherms for ethylene and ethane had highly rectangular shapes consistent with a low pressure swing capacity. Consequently, Na-ETS-10 is not readily applicable to pressure swing absorption processes (PSA), at least at lower or ambient temperatures.

However, cationic modification of as prepared Na-ETS-10 provides an adsorbent for the PSA separation of olefins and paraffins having the same number of carbon atoms, at ambient temperatures. The mono-, di- and tri-valent cations are selected from the group 2-4 metals, a proton, ammonium compounds and mixtures thereof. Some specific non-limiting examples of mono-, di-, or tri-valent cations that can be used in the current invention include, $Li^+$, $K^+$, $Cs^+$, $Mg^{2+}$, $Ca^{2+}$, $Sr^{2+}$, $Ba^{2+}$, $Sc^{3+}$, $Y^{3+}$, $La^{3+}$, $Cu^+$, $Zn^{2+}$, $Cd^{2+}$, $Ag^+$, $Au^+$, $H^+$, $NH_4^+$, and $NR_4^+$ where R is an alkyl, aryl, alkylaryl, or arylalkyl group. The cationic modifiers are generally added to unmodified Na-ETS-10 in the form of a salt or an acid. The anionic counterion associated with the cationic modifier is not specifically defined, provided that is does not adversely affect the modification (i.e. cation exchange) reactions. Suitable anions include but are not limited to acetate, carboxylate, benzoate, bromate, chlorate, perchlorate, chorite, citrate, nitrate, nitrite, sulfates, and halide (F, Cl, Br, I) and mixtures thereof. Suitable acids include inorganic and organic acids, with inorganic acids being preferred. U.S. Pat. No. 8,017,825 issued Sep. 13, 2011 to Kuznicki et al., assigned to the Governors of the University of Alberta discloses the technology, the text of which is herein incorporated by reference.

As described in U.S. Pat. No. 6,517,611, heat treatment of ETS-4 gave a controlled pore volume zeolite material, dubbed "CTS-1" which is a highly selective absorbent for olefin/paraffin separations. The CTS-1 zeolite, which has pore diameters of from about 3-4 Å, selectively adsorbed ethylene from a mixture of ethylene and ethane through a size exclusion process. The pore diameter of CTS-1, allowed diffusion of ethylene, while blocking diffusion of ethane which was too large to enter the pores of the CTS-1 zeolite, thereby providing a kinetic separation. The CTS-1 adsorbent was successfully applied to a PSA process in which ethylene or propylene could be separated from ethane or propane respectively.

The above adsorbents may be used in pressure swing adsorption units. Typically, the range of absolute pressures used during the adsorption step can be from about 10 kPa to about 2,000 kPa, (about 1.5 to about 290 pounds per square inch (psi)) preferably from about 50 kPa to about 1000 kPa (from about 7.2 to about 145 psi). The range of pressures used during the release of adsorbate (i.e. during the regeneration step) can be from about 0.01 kPa to about 150 kPa (about 0.0015 to about 22 psi), preferably from about 0.1 kPa to about 50 kPa (about 0.015 to about 7.3 psi). In general, the adsorption step can be carried out at from ambient temperatures to above about 200° C., preferably less than 150° C., most preferably less than 100° C., provided that the temperatures do not exceed temperatures at which chemical reaction of the olefin, such as a oligomerization or polymerization takes place.

Another class of adsorbents is ionic liquids. Olefins and paraffins can be separated using ionic liquids of the formula a metal dithiolene selected from the group of complexes of the formulae:

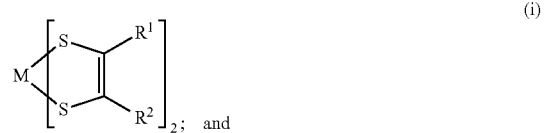

$M[S_2C_2(R^1R^2)]_2$

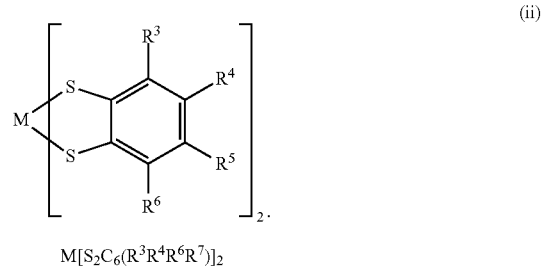

$M[S_2C_6(R^3R^4R^6R^7)]_2$ wherein M is selected from the group consisting of Fe, Co, Ni, Cu, Pd and Pt; and $R^1$, $R^2$, $R^3$, $R^4$, $R^5$, and $R^6$ are independently selected from the group consisting of a hydrogen atom, electron-withdrawing groups including those that are or contain heterocyclic, cyano, carboxylate, carboxylic ester, keto, nitro, and sulfonyl groups, hydrocarbyl radicals selected from the group consisting of $C_{1-6}$, alkyl groups, $C_{5-8}$, alkyl groups, $C_{2-8}$, alkenyl groups and $C_{6-8}$ aryl groups which hydrocarbyl radicals are unsubstituted or fully or partly substituted, preferably those substituted by halogen atoms. The ionic liquid may be used with a non-reactive solvent or co solvent. The solvent may be selected from the group conventional aromatic solvents, typically toluene. Adsorption pressures may range from 200 psig to 300 psig ($1.3 \times 10^3$ to $2 \times 10^3$ kPag), preferably below 250 psig ($1.7 \times 10^3$ kPag) and adsorption temperatures may range from ambient to 200° C., preferably below 150° C., and the olefin may be released from the ionic liquid by one or more of lowering the pressure by at least 50 psi ($3.4 \times 10^2$ kPa) and increasing the temperature by not less than 15° C.

The nitrogen from the regeneration rector, not recycled to the regeneration reactor could be used in a number of downstream unit operations. Potential downstream unit operations include an ammonia plant, an acrylonitrile plant, a urea plant and an ammonium nitrate plant.

The following non-limiting examples demonstrate the present invention. The catalyst used in the experiments was of the formula:

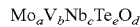

$$Mo_aV_bNb_cTe_eO_d$$

wherein:
a is from 0.90 to 1.10;
b is from 0.25 to 0.4;
c is from 0.1 to 0.3;
e is from 0.1 to 0.3; and
d is a number to satisfy the valence state of the mixed oxide catalyst.

The reactor used in the experiments consisted of a quartz tube reactor. The sample size was typically about 0.5 cm³, 0.17 g. The particle size for the catalyst was 0.2-0.7 mm.

The reactor was initially operated in a regeneration (oxidation of the catalyst) mode. The reactor was heated to a temperature from 355° C. to 397° C. in air for 30 minutes. Then the gas flow was switched to a mixture of 75 vol.-% ethane and 25 vol.-% oxygen. The flow rate of the mixture of ethane and oxygen was varied over 300/600/1200 cm³ (Stp) per hour. The reaction took place during the first minute of the passage of the reactants over the oxidized catalyst bed. The catalyst bed was then reoxidized and then a mixture of ethane and oxygen were passed over the oxidized catalyst. The gas leaving the reactor was analyzed to measure the residual oxygen and the amount of ethane, ethylene and by-products in the product gas.

Experiment #1

(Air ⇔ Gas Mixture [75% $C_2H_6$+25% $O_2$]) 355° C.

Figure 2:
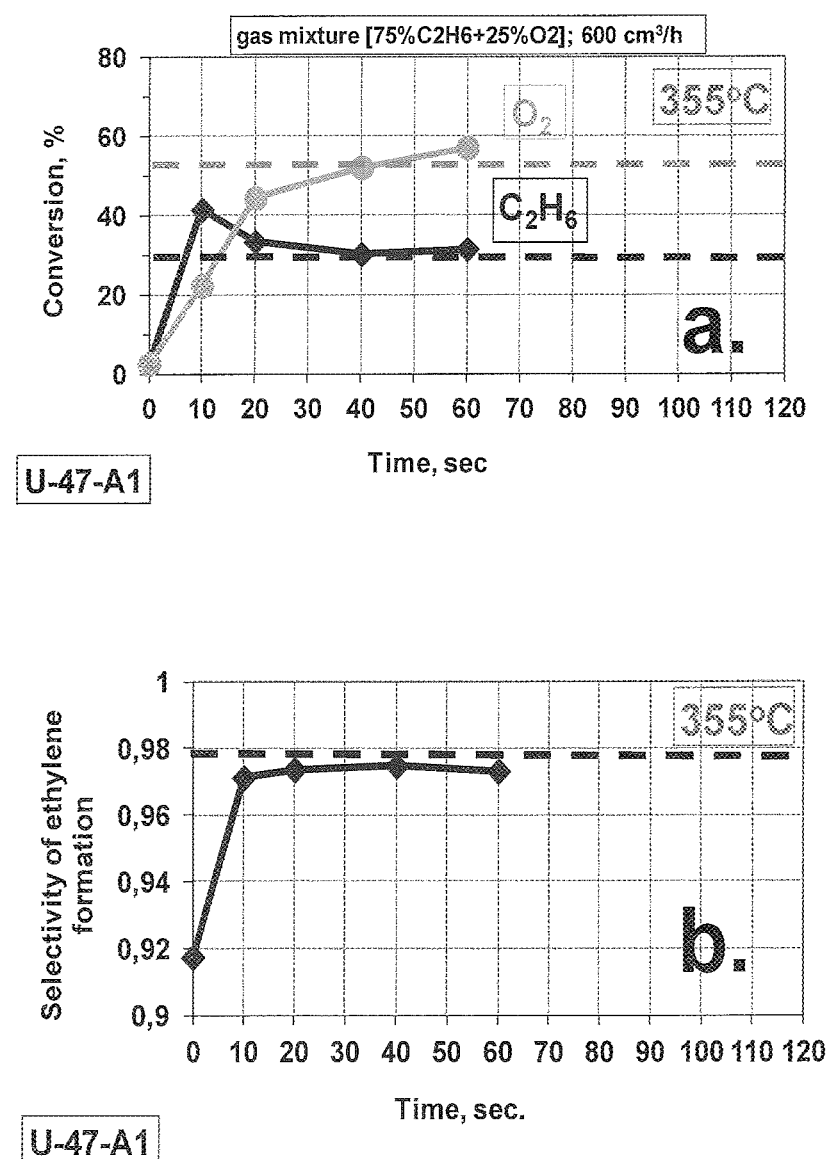
FIG. 2 a and b shows the conversion and selectivity of a feed stream comprising ethylene and 25% mole.-% of oxygen at a temperature of 355° C. in the presence of a catalyst in accordance with the present invention over a time up to 60 seconds.
Figure 3:
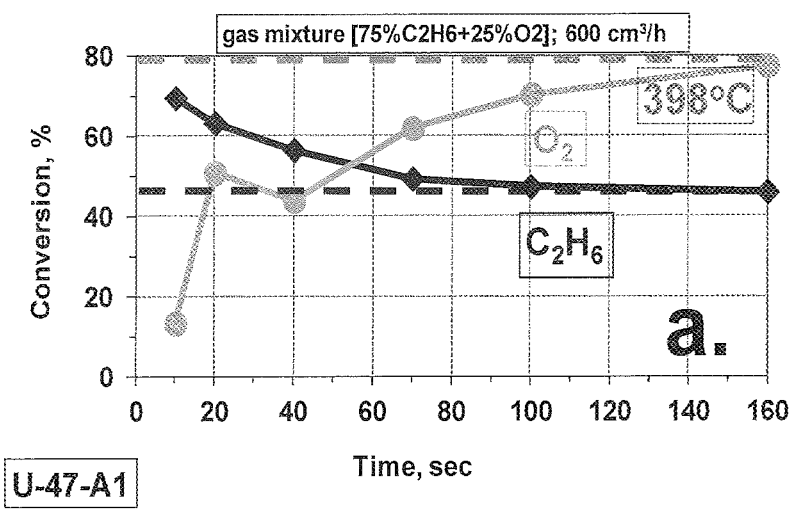
FIGS. 3 a and b shows the conversion and selectivity of a feed stream comprising ethylene and 25% mole.-% of oxygen at a temperature of 355° C. in the presence of a catalyst in accordance with the present invention over a time up to 60 seconds.
Figure 3:
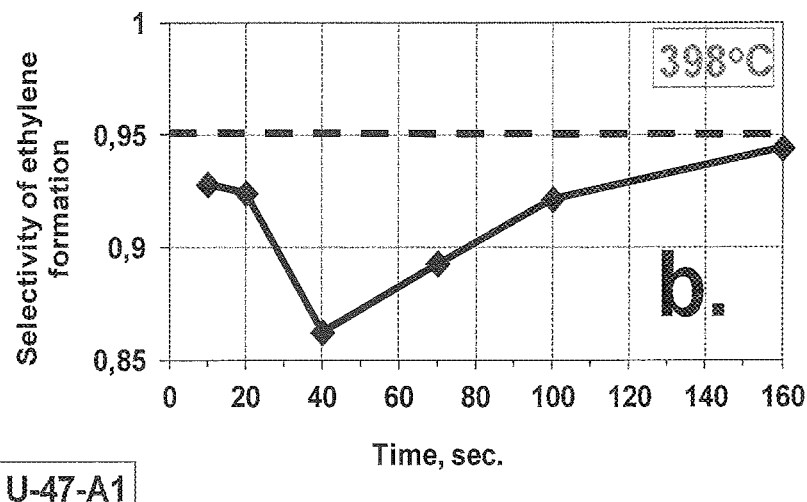

FIGS. 2 and 3 demonstrate a time dependence of the ethane and $O_2$ conversion as well as the selectivity of ethylene formation upon the gradual reduction of the pre-oxidized catalyst by the reaction mixture supplied at 600 cc/hrat two different temperatures.

As one can see (FIGS. 2, 3), all transient processes take place during the first operation minute in our testing conditions. The effect is not pronounced at ~355° C., only a slight increase of the conversion without any selectivity loss can be noted (FIG. 2). The same effect of the conversion rise becomes much stronger at 400° C., but in this case it is accompanied by a substantial loss of the selectivity due to additional formation of $CO_2$ (FIG. 3). It is necessary to mention that the more actively occurring process at 400° C. is accompanied by measurable self-heating of the catalyst layer (~5-6° C. measured on the wall of the reactor). Some contribution of undesirable complete oxidation in the gas phase cannot be excluded.

Experiment 2

Experiment 1 was repeated at 398° C.
Comparing experiment 1 and 2, the maximum conversion was increased to above 70%.

Experiment 3

Figure 4:
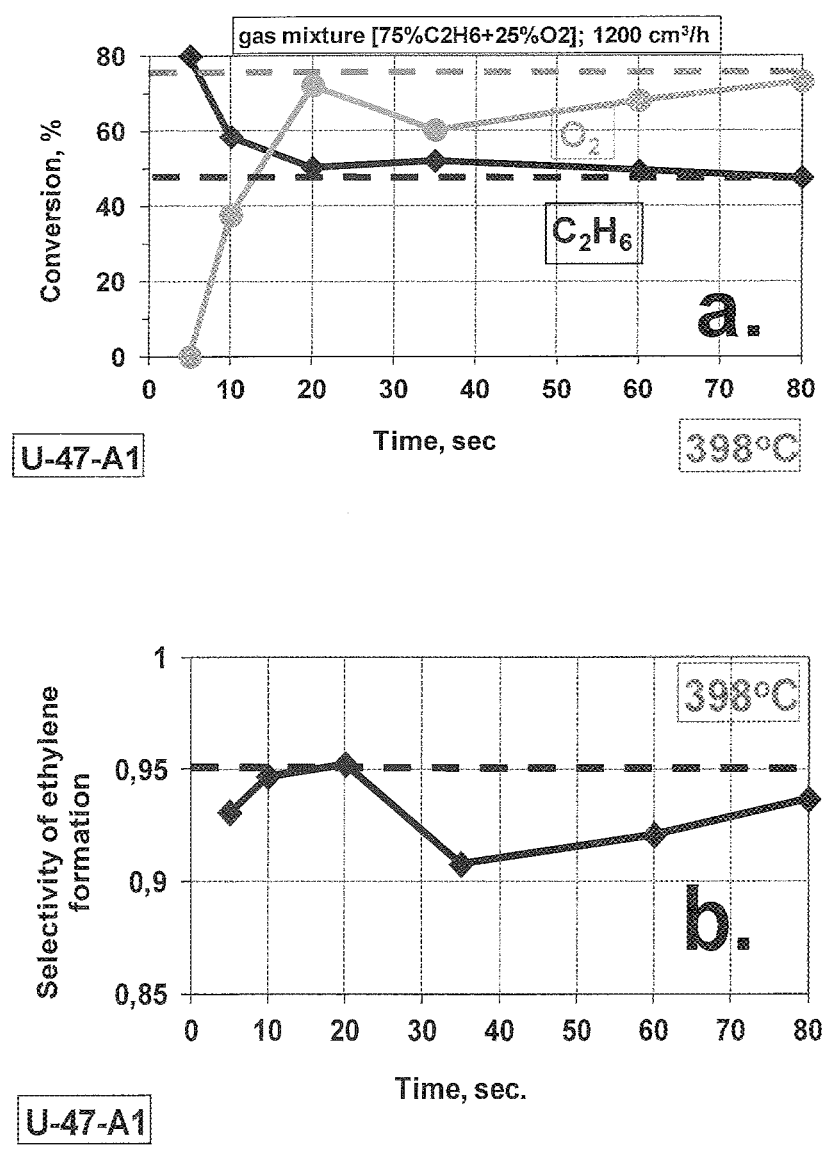
FIG. 4 is a plot showing time dependence of the ethane and O2 conversion (a) and selectivity of ethylene formation (b) after the gas flow switch [air to gas mixture] on the Mo—V—Te—Nb-Ox catalyst at 398° C. [2400 h$^{-1}$] Dotted lines correspond to the equilibrium values.

To clarify the invention, an additional test was carried out with varied gas flow rates (300 and 1200 cc/min) using same condition as example 1 and 2, except that the flow rate was 1200 cm3/h. Results obtained are presented in FIGS. 4 and 5.

Figure 5:
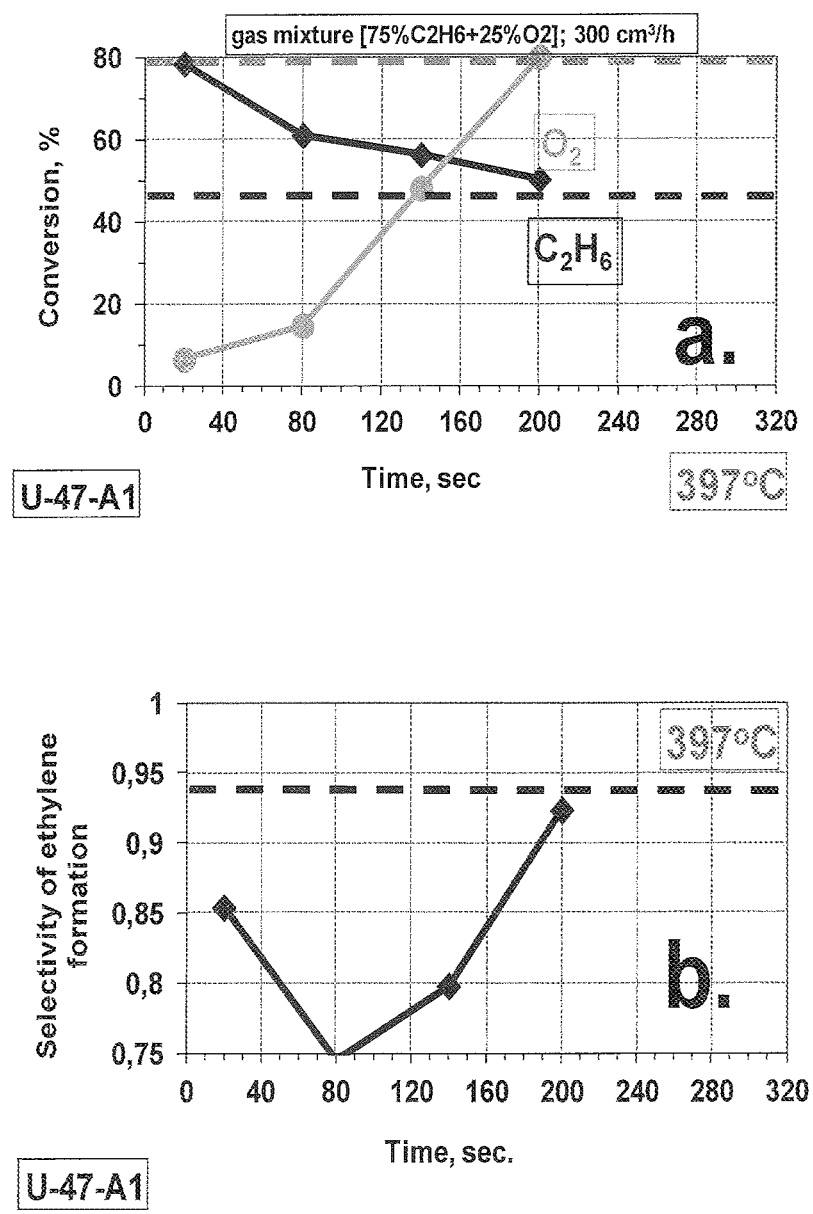
FIG. 5 is a plot showing time dependence of the ethane and O2 conversion (a) and selectivity of ethylene formation (b) after the gas flow switch [air to gas mixture] on the Mo—V—Te—Nb—Ox catalyst at 398° C. [600 h$^{-1}$] Dotted lines correspond to the equilibrium values.
Figure 6:
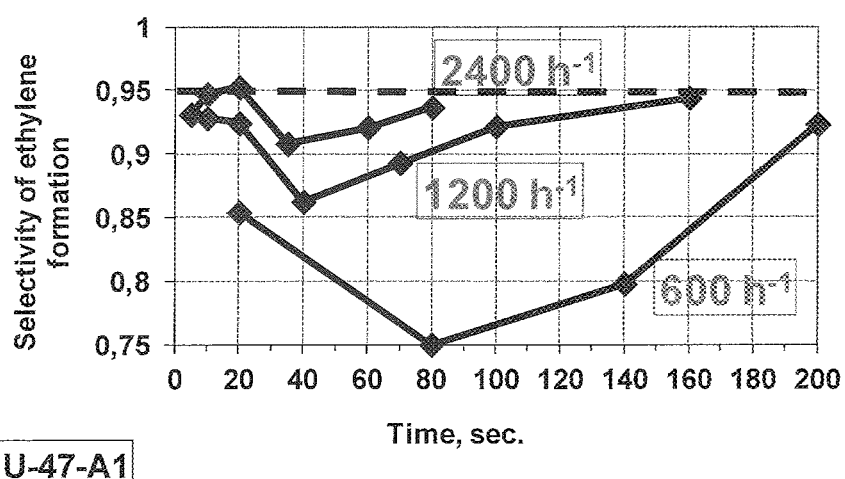
FIG. 6 is a plot showing time dependence of the selectivity of ethylene formation after the gas flow switch [air to gas mixture] on the Mo—V—Te—Nb-Ox catalyst at 398° C. at different flow rates.

The data obtained (FIGS. 3-5), shows that the selectivity is related to the feed flow rate (space velocity). Reduction of the gas flow rate down to 600 h⁻¹ causes a temporary drop of the selectivity down to 75% (FIG. 5b). Again, the process is accompanied by considerable self-heating of the catalytic layer after the gas switch to the reaction mixture (~6-7° C. measured on the wall of the reactor). The selectivity curves are summarized and compared in FIG. 6. It is interesting to note at short residence time, despite the high conversion, very little gas phase oxygen is consumed. So, the contribution of undesirable complete oxidation with temporary heating of the catalyst bed becomes more and more pronounced upon the rise of the contact time (FIG. 6). At the same time, an increase of the gas flow rate up to 2400 h⁻¹ permits us to avoid a considerable contribution of total oxidation (FIG. 6).

Figure 7:
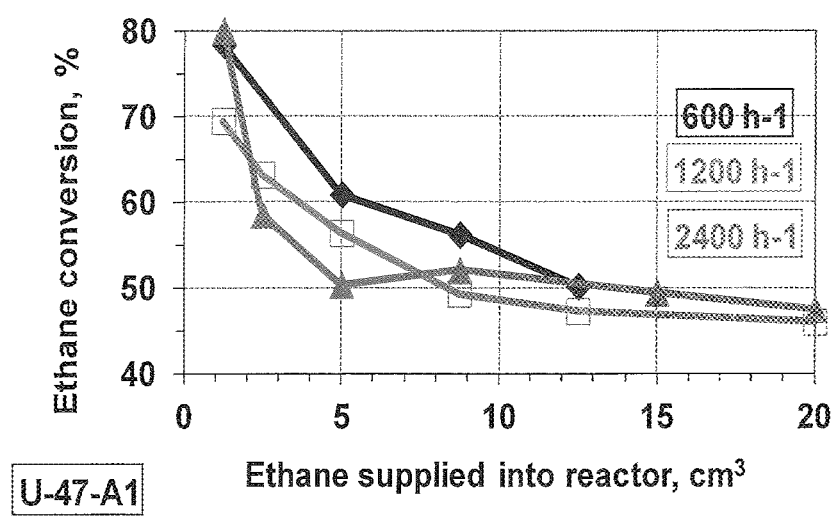
FIG. 7 is a plot showing dependence of the ethane conversion on the amount of ethane supplied into the reactor at different rates after the gas flow switch [air to gas mixture] on the Mo—V—Te—Nb-Ox catalyst at 398° C.

For quantitative comparison of the conversion data, all the results obtained at flow rates differing by a factor of 2 are presented in FIG. 7 using an absolute scale (i.e., as a function of the amount of the ethane fed through the reactor). All three curves look quite similar (FIG. 7). It is evident that the increased starting conversion of ethane (70-80%) is caused by the presence of extra-oxygen stored in the pre-oxidized catalyst, and the transient process shown in FIG. 7 is related with the gradual loss of this additional oxygen. The results obtained permit us to calculate the amount of the "reactive" lattice oxygen involved in the reaction during the transient process. Depletion of oxygen from the catalyst is the same for all three tests and can be evaluated as ~1% from the total lattice oxygen of our Mo—V—Te—Nb—$O_x$ catalyst.

Experiment 4

Periodical Redox Cycle (Pure $O_2$ ⇔ Pure $C_2H_6$): Reference Testing

Figure 8:
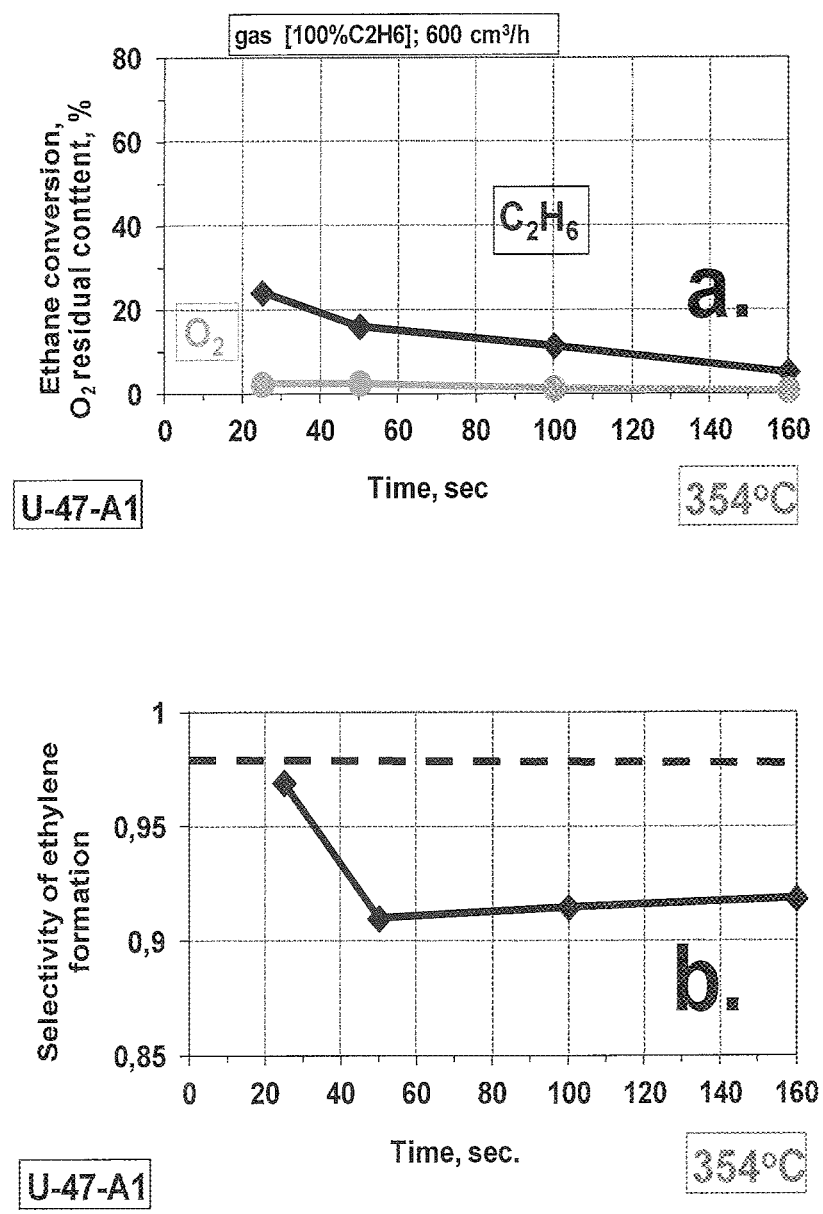
FIG. 8 is a plot showing time dependence of ethane conversion and O2 residual content (a) and selectivity of ethylene formation (b) after the gas flow switch [O2 to C2H6] on the Mo—V—Te—Nb-Ox catalyst at 355° C.
Figure 9:
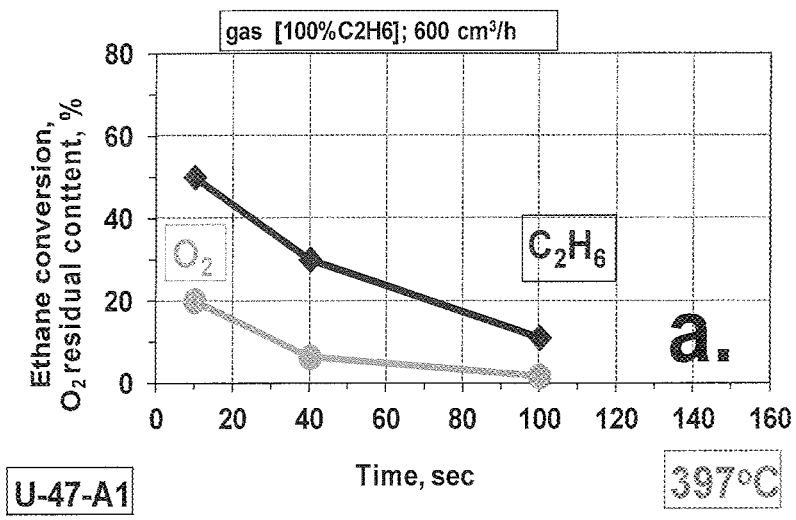
FIG. 9 is a plot showing time dependence of ethane conversion and O2 residual content (a) and selectivity of ethylene formation (b) after the gas flow switch [O2 to C2H6] on the Mo—V—Te—Nb-Ox catalyst at 397° C.
Figure 9:
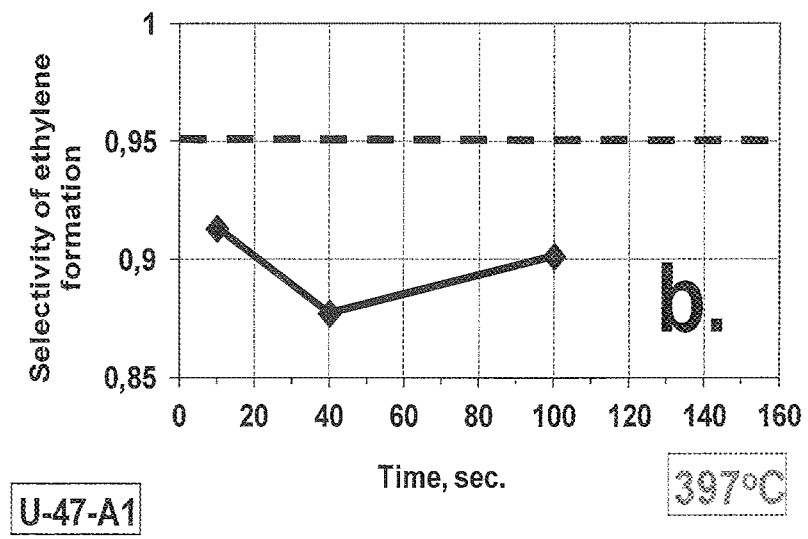

To clarify the invention, this experiment was done in the absence of oxygen in the ethane stream under the same other conditions (i.e. flow rate and temperature). In this test, the catalyst charge placed into a quartz reactor was heated to at given temperature (354° C. or 397° C.) in pure $O_2$ flow, kept for 30 min, then the gas flow (600 cm³/h) was switched to pure $C_2H_6$, and the sample of the outgoing gas was analyzed after a given time. After reoxidation of the catalyst for 30 min measurements were repeated several times with varied time interval, and resulting response curves of products were received (up to 3 min). FIGS. 8 and 9 demonstrate a time dependence of ethane conversion and residual $O_2$ content as well as selectivity of ethylene formation upon the catalyst gradual reduction by the ethane at two different temperatures.

Transient processes take place during 1-2 minutes in our testing conditions (FIGS. 8, 9). Reaction is accompanied by a measurable selectivity loss. Effect is quite pronounced even at ~350° C. (FIG. 8b) and becomes stronger at 400° C. (FIG. 9b). It is important to note that reaction is accompanied by a measurable self-heating of the catalyst layer (4-8° C. measured on the outer wall of the reactor). Back switch to $O_2$ flow for the catalyst reoxidation is also accompanied by some catalyst heating (3-4° C.). In addition, this heating seems to be non-uniform but moving throughout the layer during reaction. Taking into account that this over-heating of the catalyst is considerably stronger inside the catalyst bed the role of non-isothermal conditions provided by switch between two pure gases could be important.

The above examples also illustrates that the conversions and selectivity using a pulse mode of ODH are not as effective as a present invention.

INDUSTRIAL APPLICABILITY

The invention provides an oxidative dehydrogenation process using circulating bed reactor (similar to a fluidized bed catalyst cracker (FCC)) providing good yields of olefin product at high selectivity.

The invention claimed is:

1. A process for the oxidative dehydrogenation of one or more alkanes selected from ethane and propane in the presence of a supported catalyst chosen from:
   i) catalysts of the formula:

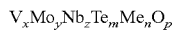

$V_xMo_yNb_zTe_mMe_nO_p$ wherein Me is a metal chosen from Ta, Ti, W, Hf, Zr, Sb and mixtures thereof; and
   x is from 0.1 to 3 provided that when Me is absent x is greater than 0.5;
   y is from 0.5 to 1.5;
   z is from 0.001 to 3;
   m is from 0.001 to 5;
   n is from 0 to 2;
   and p is a number to satisfy the valence state of the mixed oxide catalyst on a metal oxide support; and
   ii) catalysts of the formula:

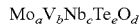

$Mo_aV_bNb_cTe_eO_d$ wherein:
   a is from 0.75 to 1.25;
   b is from 0.1 to 0.5;
   c is from 0.1 to 0.5;
   e is from 0.1 to 0.35, and
   d is a number to satisfy the valence state of the mixed oxide catalyst on a metal oxide support;
   the process comprising:
   a) passing through an oxidative dehydrogenation reactor comprising a riser containing a fluidized bed of said catalyst said one or more alkanes and oxygen at a temperature from 250° C. to 450° C., a pressure from 3.447 to 689.47 kPa (0.5 to 100 psi) and a residence time of said one or more alkanes in said riser from 0.002 to 10 seconds to produce a product stream comprising an alkene product, and reducing said catalyst, said catalyst having an average residence time in the dehydrogenation reactor of less than 30 seconds;
   b) feeding said reduced catalyst through a downcomer from said dehydrogenation reactor to a separate fluidized bed regeneration reactor and passing a stream of air optionally with additional nitrogen at a temperature from 250° C. to 400° C. and pressures from 3.447 to 689.47 kPa (0.5 to 100 psi) through said bed to oxidize said catalyst; and
   c) passing said oxidized catalyst from said fluidized bed regenerator back to said oxidative dehydrogenation riser together with steam at a temperature from 300° C. to 350° C. or atomized water at a temperature from 50° C. to 75° C. or both steam at a temperature from 300° C. to 350° C. and water at a temperature from 50° C. to 75° C.; wherein the amount of oxygen in the feed to said riser is from about 18 mole % to about 26 mole % and the conversion of alkane to alkene is not less than 50% per pass and the selectivity for the conversion of alkane to alkene is not less than 0.9.

2. The process according to claim 1, wherein the top of said riser comprises an inverted cone disperser.

3. The process according to claim 2, further comprising passing steam at a temperature from 350° C. to 450° C. counter current to the flow of oxygen depleted catalyst through said downcomer.

4. The process according to claim 3, further comprising passing air or a mixture of air and nitrogen through the regeneration reactor and generating a gas product stream comprising not less than 80-100 vol. % of nitrogen.

5. The process according to claim 4, further comprising recycling a portion of the gas product stream from the regeneration reactor to the regeneration reactor and optionally cooling the portion of the gas product stream prior to recycling.

6. The process according to claim 4, further comprising adding a CO promoter to the regenerator reactor.

7. The process according to claim 5, further comprising separating said alkene product from water in the product stream from the oxidative dehydrogenation reactor.

8. The process according to claim 7, further comprising passing nitrogen form the gas product stream from the regeneration reactor to a site integrated unit operation chosen from an ammonia plant, an acrylonitrile plant, a urea plant and, an ammonium nitrate plant.

9. The process according to claim 1, wherein the residence time of the catalyst in the regeneration reactor is less than 3 minutes.

10. The process according to claim 9, wherein the ratio of residence time of the catalyst in the regeneration reactor to the residence time of the catalyst in the oxidative dehydrogenation reactor is not less than 3.

11. The process according to claim 10, wherein the product stream from the oxidative dehydrogenation reactor and at least a portion of the gas product stream from the regenerator reactor are passed through separate steam generators to recover heat.

12. The process according to claim 11, wherein the product stream from the oxidative dehydrogenation reactor is cooled and passed through a column to separate a combustion product from the alkene product.

13. The process according to claim 11, wherein the product stream from the oxidative dehydrogenation reactor is cooled and passed through an amine unit to remove $CO_2$.

14. The process according to claim 1, wherein the support is chosen from silicon dioxide, fused silicon dioxide, aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, and yttrium oxide.

15. The process according to claim 1, wherein the alkane is ethane.

16. The process according to claim 15, wherein the catalyst is of the formula:

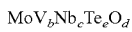

wherein:
a is 0.95 to 1.1;
b is 0.3 to 0.35;
c is 0.1 to 0.15;
e is 0.1 to 0.25; and
d is a number to satisfy the valence state of the mixed oxide catalyst on a metal oxide support.

17. The process according to claim 16, wherein in the oxidative dehydrogenation reactor the conversion to ethylene is greater than 60%.

18. The process according to claim 17, wherein in the oxidative dehydrogenation reactor the selectivity to ethylene is greater than 95%.

19. A process for the oxidative dehydrogenation of one or more alkanes selected from ethane and propane in the presence of a supported catalyst chosen from:
  i) catalysts of the formula:
    $V_xMo_yNb_zTe_mMe_nO_p$
    wherein Me is a metal chosen from Ta, Ti, W, Hf, Zr, Sb and mixtures thereof; and
    x is from 0.1 to 3 provided that when Me is absent x is greater than 0.5;
    y is from 0.5 to 1.5;
    z is from 0.001 to 3;
    m is from 0.001 to 5;
    n is from 0 to 2;
    and p is a number to satisfy the valence state of the mixed oxide catalyst on a metal oxide support; and
  ii) catalysts of the formula:

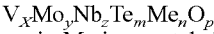

wherein:
a is from 0.75 to 1.25;
b is from 0.1 to 0.5;
c is from 0.1 to 0.5;
e is from 0.1 to 0.35, and
d is a number to satisfy the valence state of the mixed oxide catalyst on a metal oxide support;
the process comprising:
a) passing through an oxidative dehydrogenation reactor comprising a riser containing a fluidized bed of said catalyst said one or more alkanes and oxygen at a temperature from 250° C. to 450° C., a pressure from 3.447 to 689.47 kPa (0.5 to 100 psi) and a residence time of said one or more alkanes in said riser from 0.002 to 10 seconds, and reducing said catalyst, said catalyst having an average residence time in the dehydrogenation reactor of less than 30 seconds;
b) feeding said reduced catalyst through a downcomer from said dehydrogenation reactor to a separate fluidized bed regeneration reactor and passing a stream of air optionally with additional nitrogen at a temperature from 250° C. to 400° C. and pressures from 3.447 to 689.47 kPa (0.5 to 100 psi) through said bed to oxidize said catalyst; and
c) passing said oxidized catalyst from said fluidized bed regenerator back to said oxidative dehydrogenation riser together with one or more of steam at a temperature from 300° C. to 350° C. and atomized water at a temperature from 50° C. to 75° C.;
wherein the amount of oxygen in the feed to said riser is above the upper flammability limit for said feed and the conversion of alkane to alkene is not less than 50% per pass and the selectivity for the conversion of alkane to alkene is not less than 0.9;
and further wherein the top of said riser comprises an inverted cone disperser.

20. A process for the oxidative dehydrogenation of alkanes comprising:
(a) converting the alkanes to alkenes by oxidative dehydrogenation in a fluidized bed oxidative dehydrogenation reactor riser, the converting comprising passing through the oxidative dehydrogenation reactor riser a feed stream comprising the alkanes and oxygen in an amount of not less than 5 mole % and reducing catalyst particles in the fluidized bed oxidative dehydrogenation reactor riser at a temperature from 250° C. to 400° C., a pressure from 0.5 to 100 psi and a catalyst residence time of less than 30 seconds;
(b) feeding the reduced catalyst particles from the fluidized bed oxidative dehydrogenation reactor riser to a fluidized bed regeneration reactor through a first downcomer;
(c) oxidizing the reduced catalyst particles in the fluidized bed regeneration reactor at a temperature from 250° C. to 400° C., a pressure from 0.5 to 100 psi, and a catalyst residence time of less than 3 minutes, the oxidizing comprising passing through the regeneration reactor a stream comprising air through the catalyst particles in the fluidized bed regeneration reactor;
(d) feeding the oxidized catalyst particles from the fluidized bed regeneration reactor to the fluidized bed oxidative dehydrogenation reactor riser through a second downcomer; and
(e) passing a stream comprising at least one of steam and atomized water through the fluidized bed oxidative dehydrogenation reactor riser, wherein
the alkanes comprise at least one of ethane and propane;
in step (a), the conversion of the alkanes to alkenes is not less than 50% per pass and a selectivity of not less than 0.9;
a ratio of the catalyst residence time in the regeneration reactor to the residence time of the catalyst in the fluidized bed oxidative dehydrogenation reactor riser is not less than 3; and
the catalyst particles comprise catalyst selected from:

i) 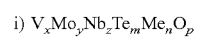

wherein Me is a metal chosen from Ta, Ti, W, Hf, Zr, Sb and mixtures thereof; and
    x is from 0.1 to 3, provided that x is greater than 0.5 when n is 0;
    y is from 0.5 to 1.5;
    z is from 0.001 to 3;
    m is from 0.001 to 5;
    n is from 0 to 2;
    and p is a number to satisfy the valence state of the mixed oxide catalyst on a metal oxide support; and ii) 

wherein:
    a is from 0.75 to 1.25;
    b is from 0.1 to 0.5;
    c is from 0.1 to 0.5;
    e is from 0.1 to 0.35, and d is a number to satisfy the valence state of the mixed oxide catalyst on a metal oxide support.

21. The process according to claim 20, wherein the oxygen in the feed stream is above 18 mole %.

22. The process according to claim 20, wherein the oxygen in the feed stream is from 5 mole % to 18 mole %.

23. The process according to claim 20, wherein the oxygen in the feed stream is from 18 mole % to 26 mole %.

24. The process according to claim 20 wherein the steam in step (e) is at a temperature of 200° C. to 400° C.

25. The process according to claim 20, wherein the atomized water in step (e) is at a temperature of 50° C. to 75° C.

\* \* \* \* \*